United States Patent [19]
Nicholas et al.

[11] Patent Number: 6,083,234
[45] Date of Patent: Jul. 4, 2000

[54] ANASTOMOSIS INSTRUMENT AND METHOD

[75] Inventors: David A. Nicholas, Trumbull; Robert C. Smith, Shelton, both of Conn.

[73] Assignee: Surgical Dynamics, Inc., Norwalk, Conn.

[21] Appl. No.: 09/256,260

[22] Filed: Feb. 23, 1999

Related U.S. Application Data

[63] Continuation-in-part of application No. 08/877,701, Jun. 17, 1997, which is a continuation-in-part of application No. 08/685,385, Jul. 23, 1996, Pat. No. 5,707,380.
[60] Provisional application No. 60/102,326, Sep. 28, 1998.

[51] Int. Cl.[7] .................................................... A61B 17/08
[52] U.S. Cl. ............................................................. 606/153
[58] Field of Search .................................... 606/142, 143, 606/151, 153, 154; 227/179, 180, 9

[56] References Cited

U.S. PATENT DOCUMENTS

| | | | |
|---|---|---|---|
| 4,299,224 | 11/1981 | Noiles ..................................... | 606/142 |
| 4,430,997 | 2/1984 | DiGiovanni et al. . | |
| 4,809,695 | 3/1989 | Gwathmey et al. . | |
| 4,983,176 | 1/1991 | Chushman et al. . | |
| 5,030,226 | 7/1991 | Green et al. ............................ | 606/158 |
| 5,188,638 | 2/1993 | Tzakis ..................................... | 606/153 |
| 5,340,360 | 8/1994 | Stefanchik ............................... | 606/142 |
| 5,366,462 | 11/1994 | Kaster et al. ............................ | 606/153 |
| 5,403,333 | 4/1995 | Kaster et al. ............................ | 606/153 |
| 5,443,198 | 8/1995 | Viola et al. .............................. | 227/179 |
| 5,501,698 | 3/1996 | Roth et al. ............................... | 606/205 |

*Primary Examiner*—Gary Jackson

[57] ABSTRACT

A surgical instrument for performing an anastomosis includes a housing having a proximal end and a distal end; a shaft extending from the housing distal end; and a disposable loading unit configured and dimensioned to retain a plurality of surgical fasteners, the disposable loading unit extending from the shaft and forming a juncture with the shaft, the disposable loading unit including: i) opposed split-sections pivotably connected to facilitate movement of the opposed split-sections between open and closed configurations, the opposed split sections being movable through a firing stroke from a first position to a second position and back to the first position to form a plurality of surgical fasteners; and ii) a pivot lockout member including a latch portion which extends between the opposed split-sections, the latch portion including a contact surface which interacts with a corresponding surface formed on at least one of the opposed split-sections to retain the opposed split-sections in the closed configuration, wherein upon return of the fastener pusher member to the first position from the second position, the pivot lockout member is displaced relative to the opposed split sections to an unlocked configuration.

27 Claims, 24 Drawing Sheets

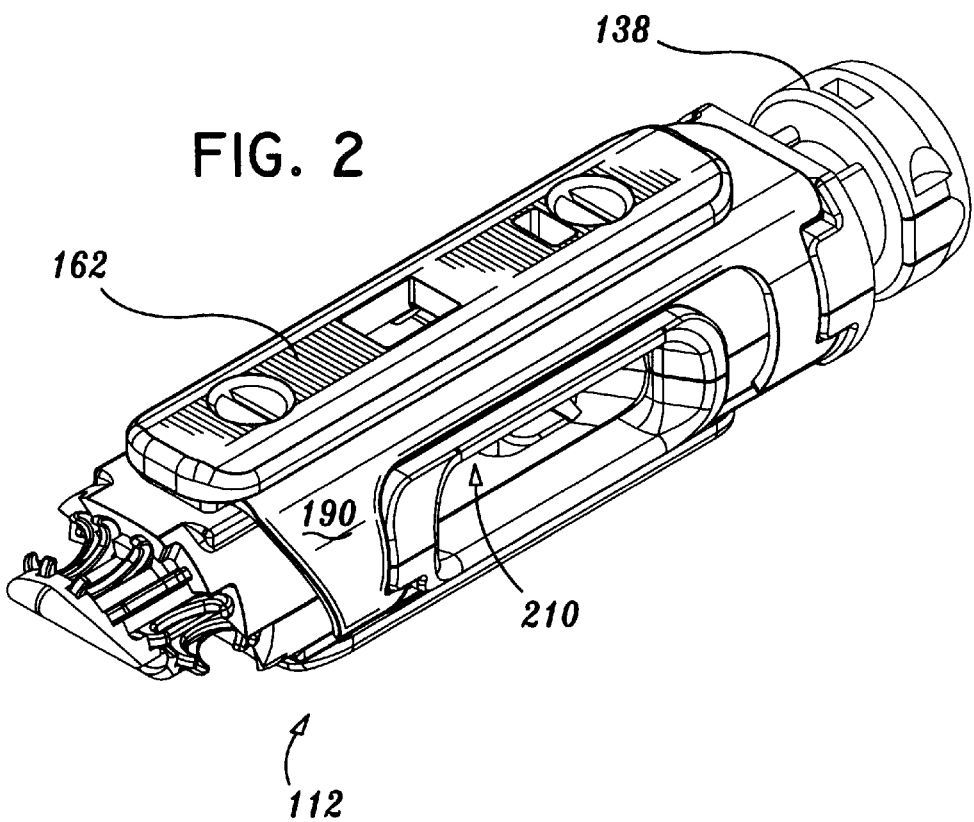
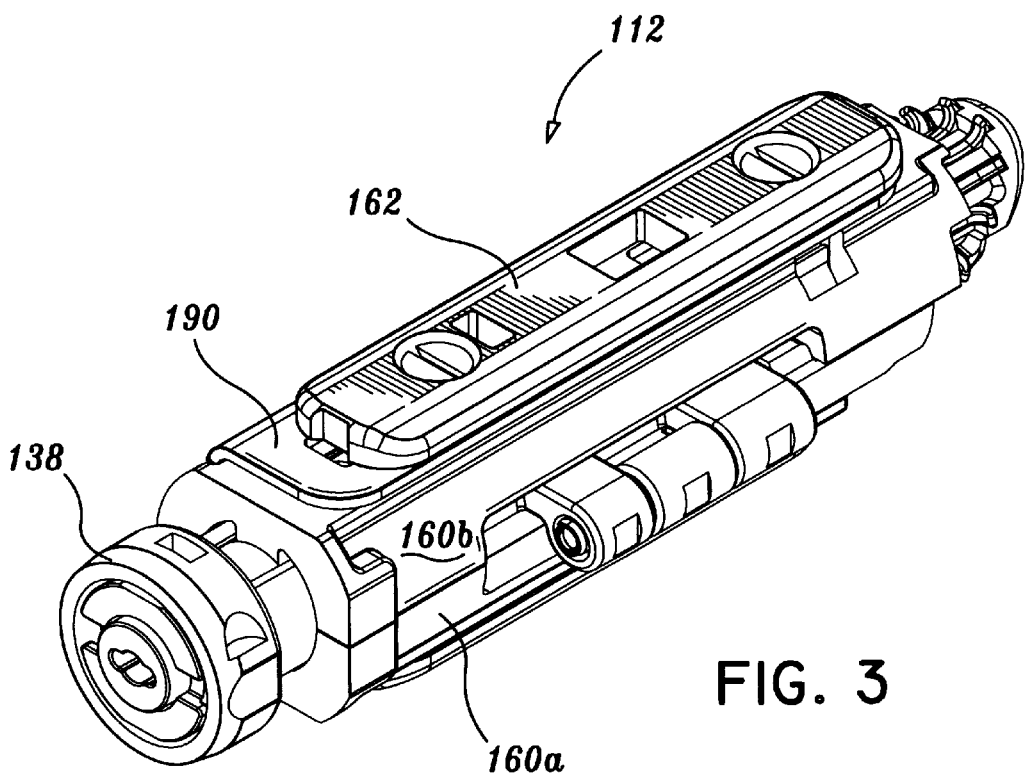

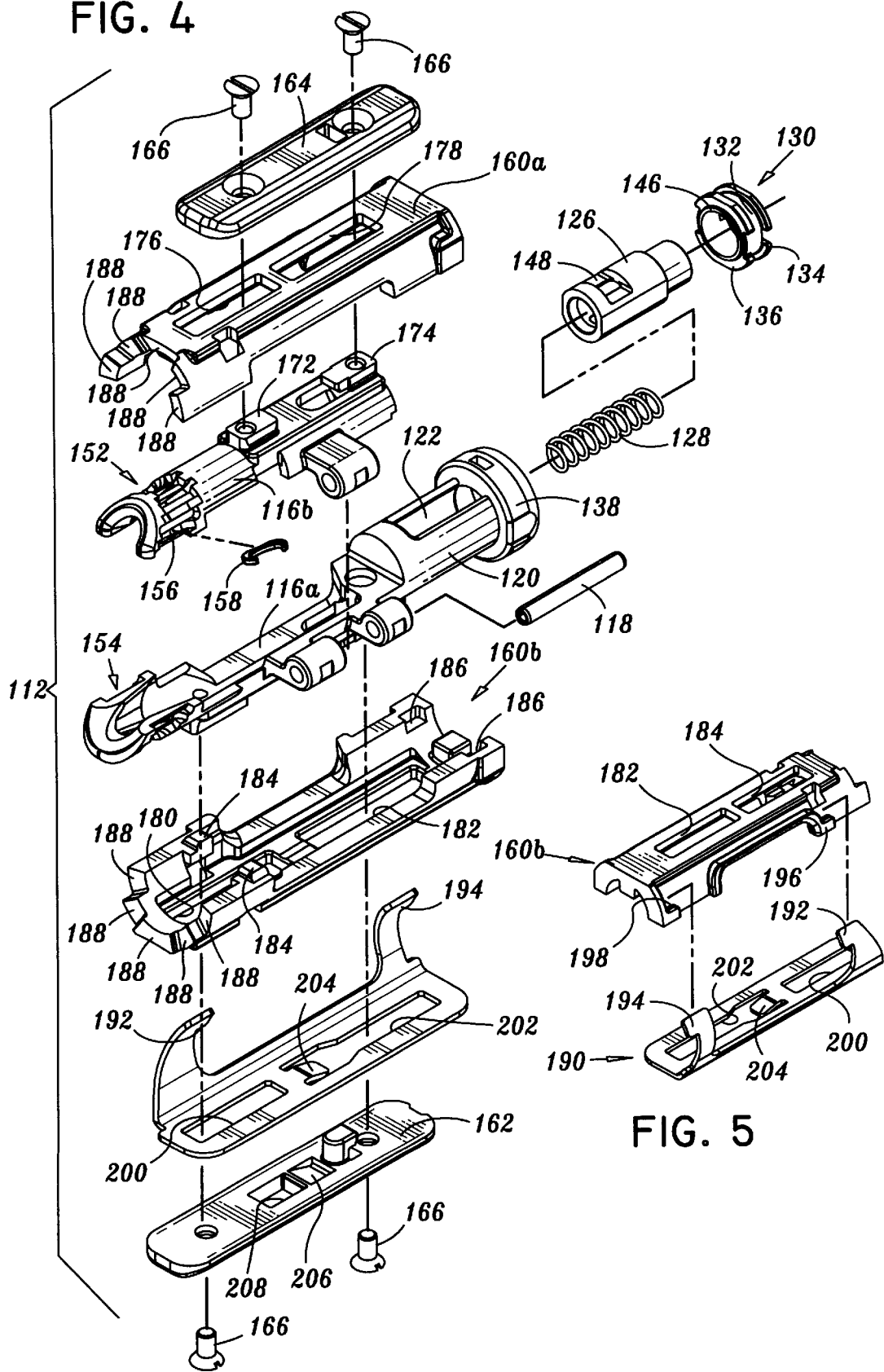

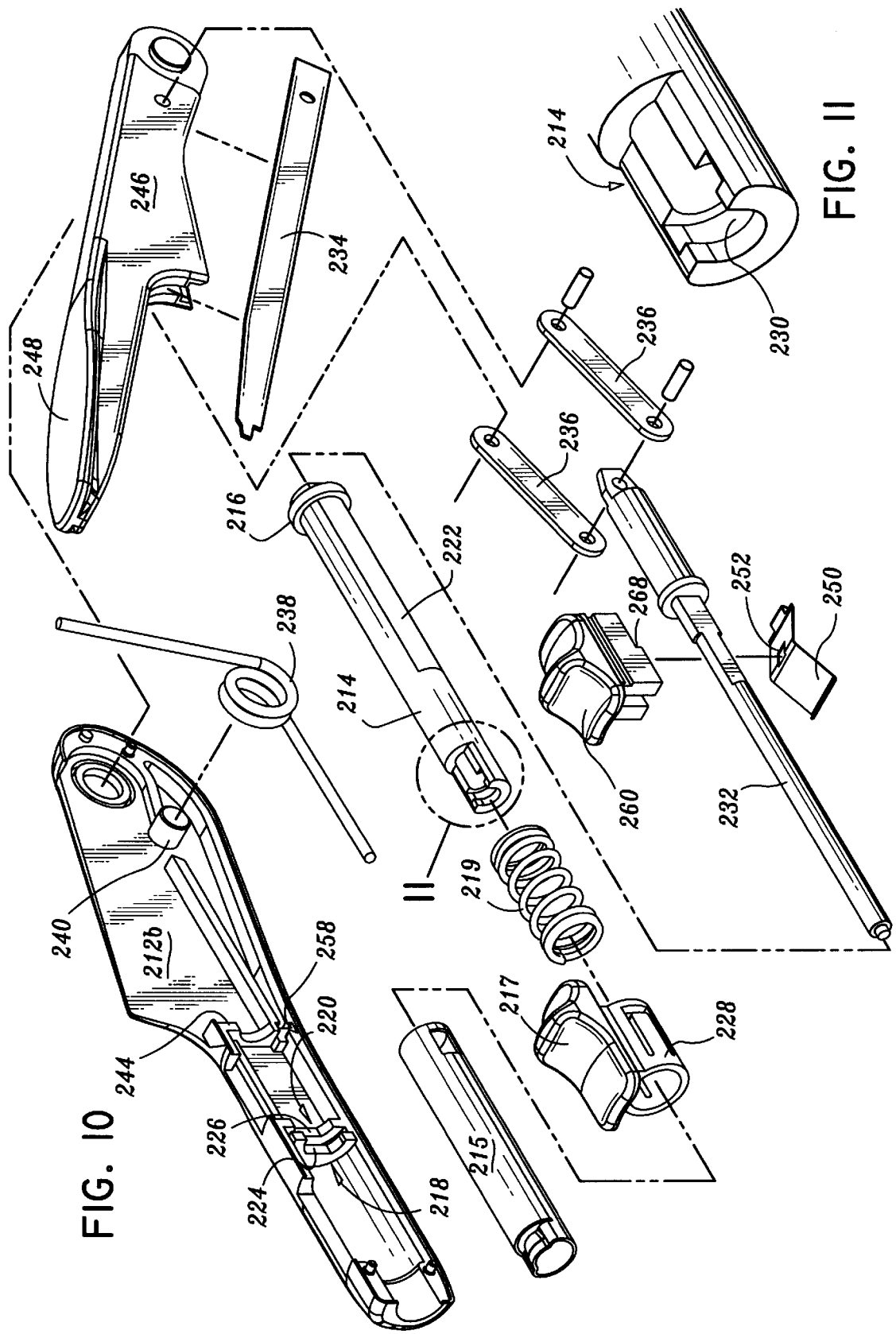

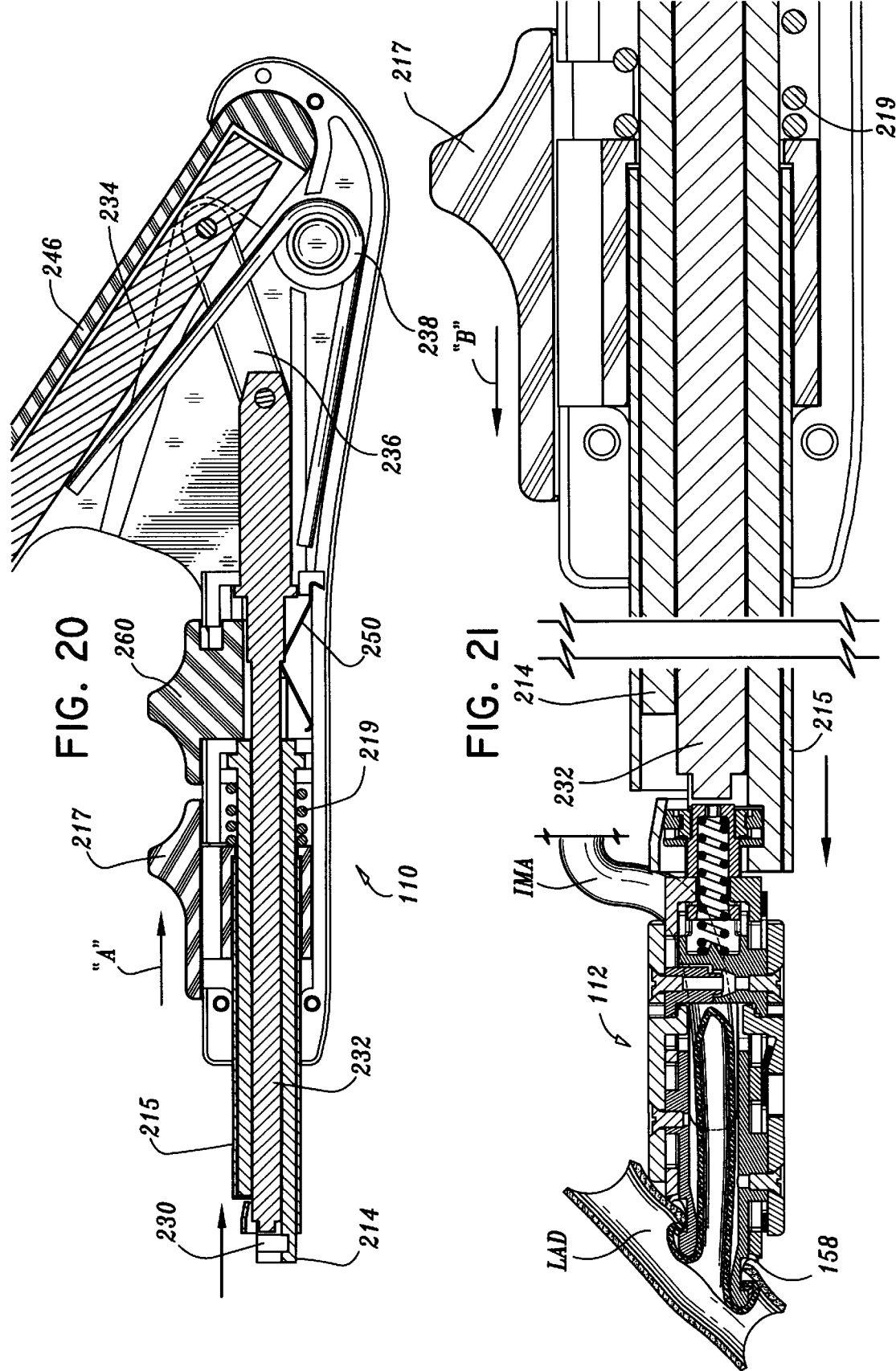

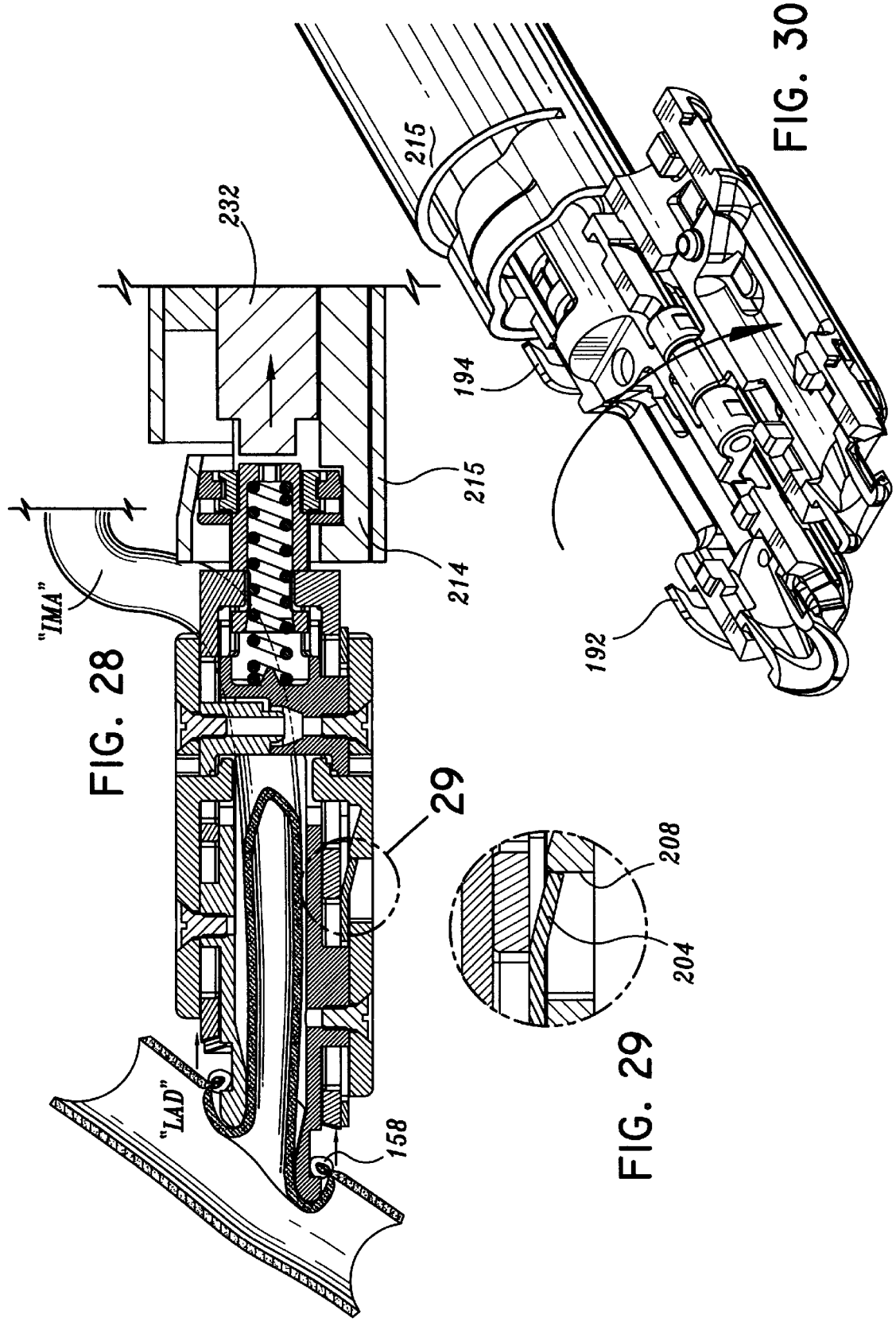

ANASTOMOSIS INSTRUMENT AND METHOD

CROSS REFERENCE TO RELATED APPLICATIONS

This application is a continuation-in-part of U.S. Application Ser. No. 08/877,701, entitled "Singleshot Anastomosis Instrument With Detatchable Loading Unit and Method", which was filed Jun. 17, 1997 by Manzo et al., which application is a continuation-in-part of U.S. Application Ser. No. 08/685,385, entitled "Anastomosis Instrument and Method", filed Jul. 23, 1996 by Hinchliffe et al., now U.S. Pat. No. 5,707,380, the entire contents of both of these disclosures are hereby incorporated by reference. This application also claims priority from U.S. Provisional Application Ser. No. 60/102,326 which was filed on Sep. 28, 1998.

BACKGROUND

1. Technical Field

The present disclosure relates to a surgical instrument and method for performing anastomosis of tubular body structures, and more particularly to an instrument for performing vascular anastomoses.

2. Background of Related Art

Anastomoses of tubular body structures may be performed for a number of different procedures. One general example of an anastomosis is a vascular anastomosis wherein two blood vessels are joined together to permit blood flow therebetween. A specific example of vascular anastomosis is an arteriovenous fistula ("A-V fistula") which is performed to facilitate hemodialysis for end stage kidney disease. The procedure usually consists of an end to side anastomosis joining an artery and a vein in the forearm, e.g., joining the radial artery end to side with the cephalic (radial) vein or the ulnar artery with the basilic (ulnar) vein. It can also be performed in the leg, but usually after all the arm sites have been exhausted. The A-V fistula allows a single puncture at the dialysis unit for blood cleansing. The fistula allows a greater flow and outflow rate through the dialyzer.

Another specific example of a vascular anastomosis is a coronary artery bypass graft ("CABG"). Coronary artery disease is often characterized by lesions or occlusions in the coronary arteries which may result in inadequate blood flow to the myocardium, or myocardial ischemia, which is typically responsible for such complications as angina pectoris, necrosis of cardiac tissue (myocardial infarction), and sudden death. In some cases, coronary artery disease may be treated by the use of drugs and by modifications in behavior and diet. In other cases, dilatation of coronary arteries may be achieved by such procedures as angioplasty, laser ablation, atherectomy, catheterization, and intravascular stents.

For certain patients, a CABG procedure is the preferred form of treatment to relieve symptoms and often increase life expectancy. A CABG procedure consists of direct anastomosis of a vessel segment to one or more of the coronary arteries. For example, a reversed segment of the saphenous vein may be grafted at one end to the ascending aorta as an arterial blood source and at the other end to a coronary artery at a point beyond the arterial occlusion. Alternatively, the internal mammary artery (IMA) is located in the thoracic cavity adjacent the sternum and is likewise suitable for grafting to a coronary artery, such as the left anterior descending artery (LAD).

The performance of a CABG procedure typically requires access to the heart, blood vessels and associated tissue. Access to the patient's thoracic cavity may be achieved in an open procedure by making a large longitudinal incision in the chest. This procedure, referred to as a median sternotomy, requires a saw or other cutting instrument to cut the sternum and allow two opposing halves of the rib cages to be spread apart. U.S. Pat. No. 5,025,779 to Bugge discloses a retractor which is designed to grip opposite sternum halves and spread the thoracic cavity apart. The alarge opening which is created by this technique enables the surgeon to directly visualize the surgical site and perform procedures on the affected organs. However, such procedures that involve large incisions and substantial displacement of the rib cage are often traumatic to the patient with significant attendant risks. The recovery period may be extensive and is often painful. Furthermore, patients for whom coronary surgery is indicated may need to forego such surgery due to the risks involved with gaining access to the heart.

U.S. Pat. No. 5,503,617 to Jako discloses a retractor configured to be held by the surgeon for use in vascular or cardiac surgery to retract and hold ribs apart to allow access to the heart or a lung through an operating "window". The retractor includes a rigid frame and a translation frame slidably connected to the rigid frame. Lower and upper blades are rotatably mounted to the rigid frame and the translation frame respectively. The "window" approach enables the surgeon to gain access through a smaller incision and with less displacement of the ribs, and consequently, less trauma to the patient.

Once access to the thoracic cavity has been achieved, surgery on the heart may be performed. Such procedures typically require that the heart beat be arrested while maintaining circulation throughout the rest of the body. Cardioplegic fluid, such as potassium chloride (KCl) is delivered to the blood vessels of the heart to paralyze the myocardium. As disclosed in WO 95/15715 to Sterman et al. for example, cardioplegic fluid is infused into the myocardium through the coronary arteries by a catheter inserted into the ascending aorta. Alternatively, cardioplegic fluid is infused through the coronary veins in a retrograde manner by a catheter positioned in the interior jugular vein accessed at the patient's neck. Such procedures require the introduction of multiple catheters into the blood vessels adjacent the heart, which is complicated procedure requiring that the desired vessels be properly located and accessed. The progression of the guide wires and catheters must be closely monitored to determine proper placement. Furthermore, the introduction of catheters forms punctures in the blood vessels that must be subsequently closed, and there is an increased risk of trauma to the interior walls of the vessels in which the catheters must pass.

Alternatively, the CABG procedure may be performed while the heart is permitted to beat. Such a procedure is now commonly referred to as minimally invasive direct coronary artery bypass (MIDCAB). A surgical instrument is used to stabilize the heart and restrict blood flow through the coronary artery during the graft procedure. Special care must be given to procedures performed on a beating heart, e.g. synchronizing procedures to occur at certain stages in the cardiac cycle, such as between heartbeats.

To perform a CABG procedure, the harvested vessel segment, such as the IMA, is grafted to the coronary artery by end-to-side anastomosis. Typically, sutures are used to graft the vessel segments. However, conventional suturing is complicated by the use of minimally invasive procedures, such as the window approach. Limited access and reduced visibility may impede the surgeon's ability to manually apply sutures to a graft. Additionally, it is difficult and time consuming to manually suture if the CABG procedure is being performed while the heart is beating as the suturing must be synchronized with the heart beat.

The process of manually suturing the harvested vessel segment to a coronary artery is time consuming and requires a great deal of skill on the part of the surgeon. The resulting sutured anastomosis will also be dependent on the skills of the surgeon. In minimally invasive procedures such as in MIDCAB, the ability to suture is even more complicated due to limited maneuverability and reduced visibility. U.S. Pat. No. 5,707,380 to which issued on Jan. 3, 1998 to Hinchliffe et al., the entire contents of which are hereby incorporated by reference, discloses an apparatus and a procedure that enables the remote anastomosis without piercing of vessels during both conventional and minimally invasive procedures. A continuing need exists, however, for improved surgical instruments and methods for performing remote anastomoses during both conventional and minimally invasive procedures.

SUMMARY

The present disclosure provides a surgical instrument for performing an anastomosis, which includes a housing having a proximal end and a distal end; a shaft extending from the housing distal end; and a disposable loading unit configured and dimensioned to retain a plurality of surgical fasteners, the disposable loading unit extending from the shaft and forming a juncture with the shaft, the disposable loading unit including: i) opposed split-sections pivotably connected to facilitate movement of the opposed split-sections between open and closed configurations, the opposed split sections being movable through a firing stroke from a first position to a second position and back to the first position to form a plurality of surgical fasteners; and ii) a pivot lockout member including a latch portion which extends between the opposed split-sections, the latch portion including a contact surface which interacts with a corresponding surface formed on at least one of the opposed split-sections to retain the opposed split-sections in the closed configuration, wherein upon return of the fastener pusher member to the first position from the second position, the pivot lockout member is displaced relative to the opposed split sections to an unlocked configuration.

A lock member is disposed relative to the juncture of the disposable loading unit and the shaft, the lock member operable from the housing and movable between an unlocked position wherein the disposable loading unit is unsecured relative to the shaft and a locked position wherein the disposable loading unit is secured relative to the shaft. The lock member may further be biased towards the locked position.

An actuator lever is disposed on the housing and operatively associated with the opposed split sections such that movement of the actuator lever from an initial position to a secondary position effects movement of the opposed split sections being from the first position to the second position to effect deformation of the plurality of surgical fasteners.

A firing safety assembly is provided which operatively interacts with the actuator lever to prevent unintended movement of the actuator lever from the initial position to the secondary position. The firing safety assembly is normally biased towards a locked out configuration.

In a particular aspect of the present disclosure, the shaft and the disposable loading unit each define respective central longitudinal axes which are substantially axially aligned with each other.

In a further embodiment of the present disclosure, a surgical instrument for performing an anastomosis is provided which includes a housing having a proximal end and a distal end, a shaft extending from the housing distal end; a disposable loading unit rotatably and detachably extending from the shaft and forming a juncture with the shaft, the disposable loading unit including: i) a fastener support member configured and dimensioned to support a plurality of surgical fasteners in a predetermined array of a generally close-ended geometric configuration; and ii) a fastener pusher member disposed adjacent the fastener support member, the fastener pusher member being movable from a first position relative to the plurality of surgical fasteners to a second position relative to the plurality of surgical fasteners so as to deform the plurality of surgical fasteners to a tissue gripping orientation; and a lock member disposed relative to the juncture of the disposable loading unit and the shaft, the lock member operable from the housing and movable between an unlocked position wherein the disposable loading unit is unsecured relative to the shaft and a locked position wherein the disposable loading unit is secured relative to the shaft.

An actuator lever is disposed on the housing and operatively associated with the fastener pusher member such that movement of the actuator lever from an initial position to a secondary position effects movement of the fastener pusher member from the first position to the second position to effect deformation of the plurality of surgical fasteners.

An actuator rod is also provided which is connected to the actuator lever and wherein the disposable loading unit further includes an actuator member which interacts with the actuator lever to effect movement of the fastener pusher member from the first position to the second position to effect deformation of the surgical fasteners.

A firing safety assembly is also provided which operatively interacts with the actuator lever to prevent unintended movement of the actuator lever from the initial position to the secondary position. The firing safety assembly may normally be biased towards a locked out configuration.

In a particular aspect of the present disclosure, the shaft and the fastener pusher member each define respective central longitudinal axes which are substantially axially aligned with each other.

In another aspect of the present disclosure, the fastener support member and the fastener pusher member are each formed of respective opposing split-sections, at least two of the split-sections being pivotably connected to facilitate movement of the opposed split-sections between open and closed configurations. A pivot lockout member is also provided which extends between the opposed split-sections and includes a contact surface which interacts with a corresponding surface formed on at least one of the opposed split-sections to retain the opposed split-sections in the closed configuration. Optionally, the fastener pusher member is biased to return to the first position after movement to the second position. A particular feature of the present disclosure is that upon return of the fastener pusher member to the first position from the second position, the pivot lockout member is displaced to an unlocked configuration.

In a further alternative embodiment, the present disclosure also provides a disposable loading unit for a surgical anastomosis instrument, which includes an elongated fastener support member defining a pathway extending at least partially therethrough and including a first opening at a distal end thereof and a second opening spaced from the distal end and in communication with the pathway, the second opening configured and dimensioned to receive a tubular vessel therethrough such that the tubular vessel can pass through the pathway and extend outward from the first opening at the distal end, the fastener support member further including a plurality of spaced apart retention slots defined therein, each retention slot being adapted to support a respective surgical fastener of a plurality of surgical fasteners; a fastener pusher member disposed adjacent the fastener support member, the fastener pusher member movable from a first position relative to the plurality of surgical fasteners to a second position relative to the plurality of surgical fasteners so as to deform the plurality of surgical fasteners; an actuator operatively associated with the fastener pusher member to effect movement of the fastener pusher member from the first position to the second position; and a mounting hub disposed adjacent the actuator and defining an access opening, such that a portion of the actuator is accessible through the access opening, the mounting hub being configured and dimensioned to be removably and rotatably attached to a distal portion of the surgical instrument thereby facilitating removable attachment of the disposable loading unit to the surgical instrument.

In one aspect of the embodiment, the fastener support member and the fastener pusher member are each formed of respective opposing split-sections, at least two of the split-sections being pivotably connected to facilitate movement of the opposed split-sections between open and closed configurations. A further feature of the embodiment is a pivot lockout member which extends between the opposed split-sections and includes a contact surface which interacts with a corresponding surface formed on at least one of the opposed split-sections to retain the opposed split-sections in the closed configuration. In a further aspect of the embodiment, the fastener pusher member is biased to return to the first position after movement to the second position. In a further unique feature of the present disclosure, upon return of the fastener pusher member to the first position from the second position, the pivot lockout member is displaced to an unlocked configuration.

The present disclosure also provides a method of performing a vascular anastomosis which includes the steps of providing a disposable loading unit having a fastener support member defining a passage therethrough for reception of a first vessel, a plurality of surgical fasteners supported by the fastener support at a distal end thereof; positioning an end of the first vessel through the passage and everting the end of the vessel over the distal end of the fastener support adjacent the plurality of surgical fasteners; engaging the first vessel with the surgical fasteners; inserting the distal edge of the fastener support into an opening in a side wall of a second vessel; engaging the side wall of the second vessel with the surgical fasteners adjacent the opening; connecting the disposable loading unit to an actuator handle assembly after step e) such that the disposable loading unit is rotatable with respect to the actuator handle assembly; and deforming the legs of each surgical fastener by actuation of the actuator handle assembly to secure the first and second vessels together in fluid communication with each other.

In a further aspect of the presently disclosed method, an additional step is provided of removing the first vessel from the disposable loading unit by opening a split-section of the disposable loading unit.

BRIEF DESCRIPTION OF THE DRAWINGS

An illustrative embodiment of the subject surgical instrument and method are described herein with reference to the drawings wherein:

FIG. 2 is a perspective view of a disposable loading unit constructed in accordance with a preferred embodiment of the present disclosure;

FIG. 3 is a perspective view of the disposable loading unit of FIG. 2 as seen from a reverse angle;

FIG. 4 is a perspective view the disposable loading unit embodiment of FIG. 2 shown with parts separated;

FIG. 5 is a perspective view of a fastener pusher half-section and a hinge lock the embodiment of the disposable loading unit of FIG. 2;

FIG. 10 is a perspective view of the handle/actuator assembly of FIG. 9 shown with parts separated;

FIG. 11 is an enlarged view of the distal end of a disposable loading unit holding tube;

FIG. 20 is a horizontal cross-sectional view of the handle/actuator assembly;

FIG. 21 is a partial horizontal cross-sectional view showing a locking mechanism to secure the disposable loading unit to the handle/actuator assembly;

FIG. 28 is a horizontal cross-sectional view, which shows retraction of an actuator rod of the handle/actuator assembly and lockout of a hinge lock on the disposable loading unit;

FIG. 29 is an enlarged view of the indicated area of detail of FIG. 28;

FIG. 30 is a perspective view of the distal end of the surgical instrument showing the opening of the disposable loading unit;

DETAILED DESCRIPTION OF PREFERRED EMBODIMENTS

Preferred embodiments of the surgical instrument and method disclosed herein will be described in terms of a minimally invasive direct coronary artery bypass (MIDCAB) procedure wherein a vascular anastomosis is created by joining a section of a harvested vessel, e.g., the internal memory artery (IMA) to bypass an occlusion in a coronary artery, e.g., the left anterior descending artery (LAD). However, the presently disclosed surgical anastomosis instrument may also be utilized in performing anastomosis of other tubular luminal body structures. For example, the presently disclosed surgical anastomosis instrument may also be utilized to perform an A-V fistula to facilitate hemodialysis. This procedure consists of an end-to-side anastomosis joining an artery and a vein in the forearm or near the elbow. The A-V fistula allows a single puncture at the dialysis unit for blood cleansing.

Figure 1:
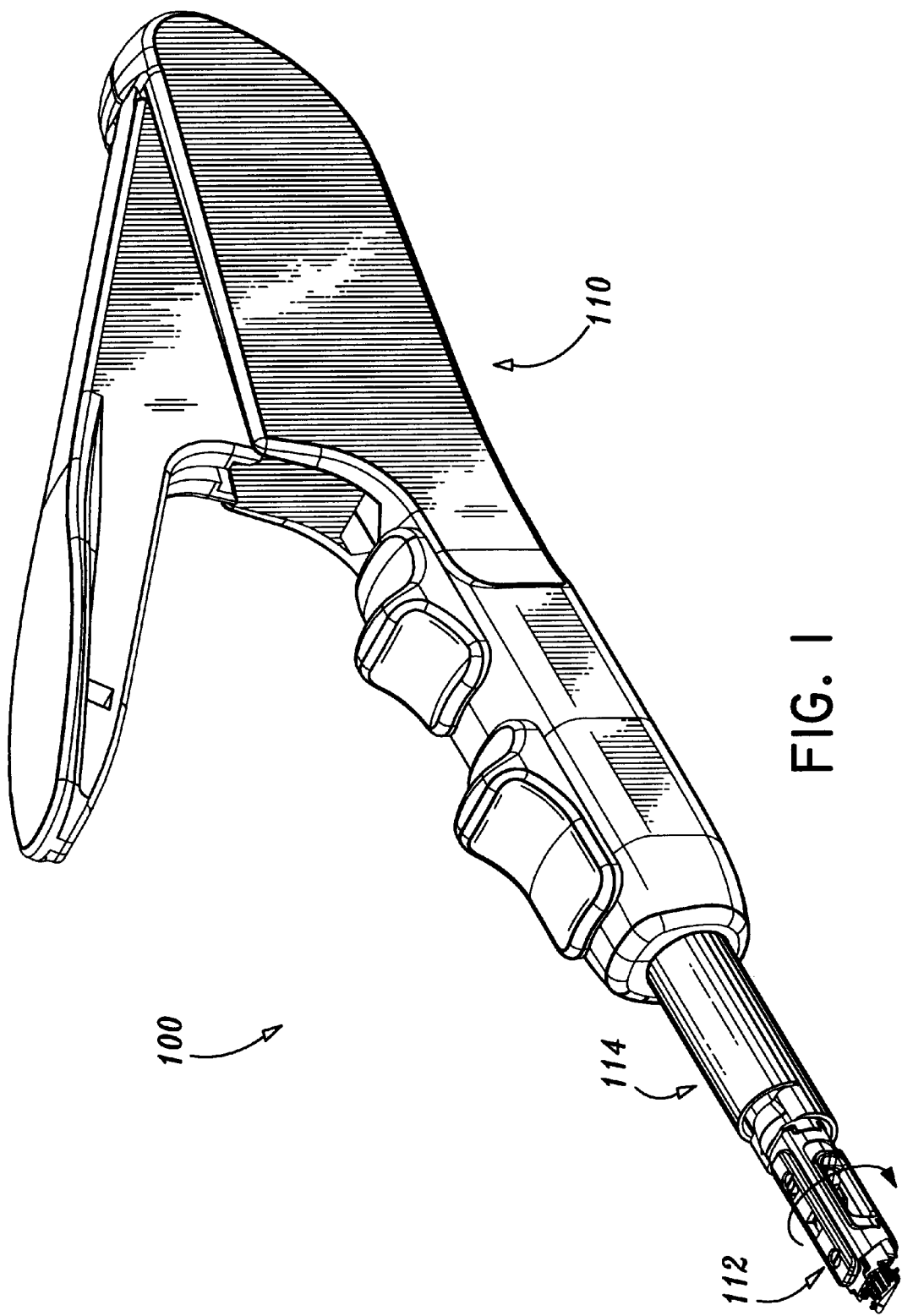
FIG. 1 is a perspective view of a surgical instrument constructed in accordance with a preferred embodiment of the present disclosure.
Figure 6:
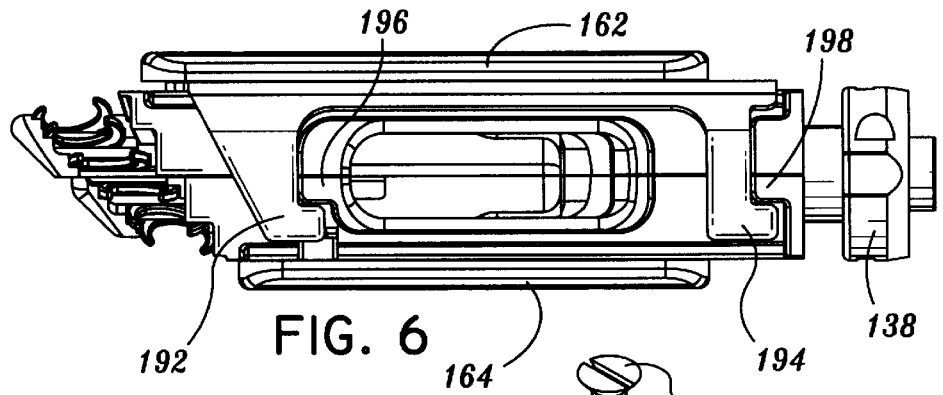
FIG. 6 is a side view of the disposable loading unit of the embodiment of FIG. 2.
Figure 7:
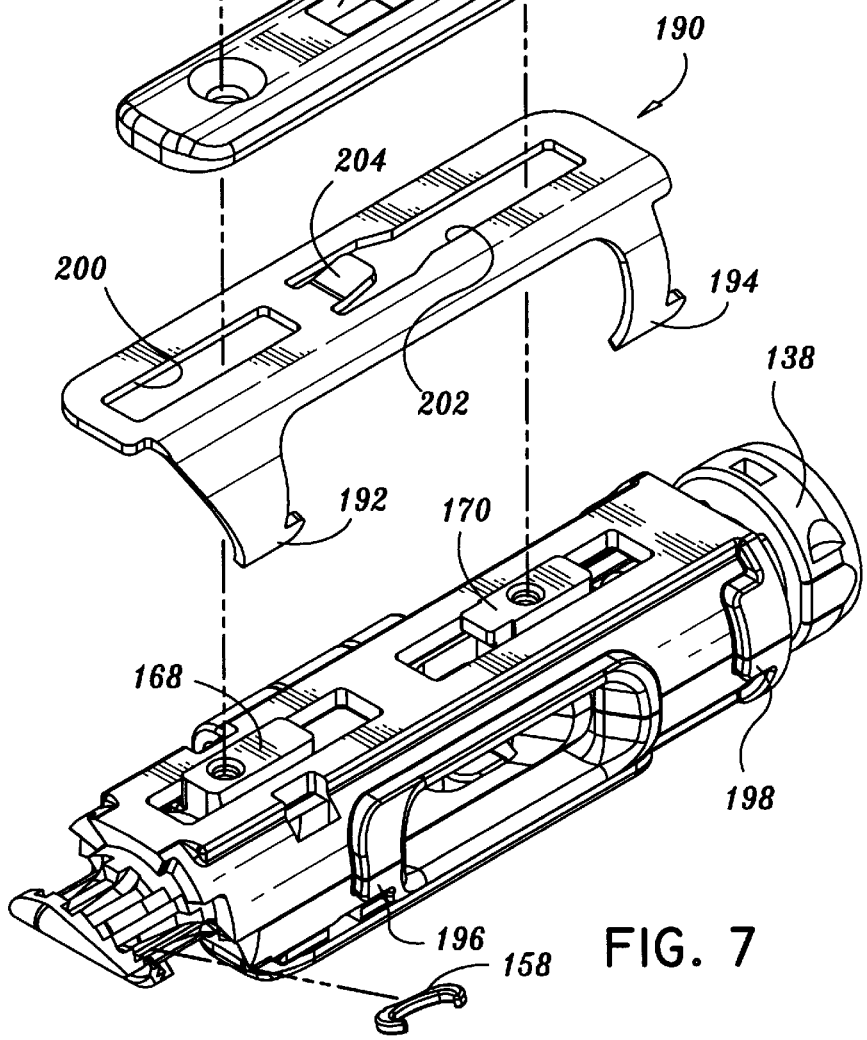
FIG. 7 is a perspective view of the disposable loading unit of the embodiment of FIG. 2 showing a hinge lock and a cover plate separated.

Referring now in detail to the drawing figures in which like reference numerals identify similar or identical elements, one embodiment of the present disclosure is illustrated generally in FIG. 1 and is designated therein as surgical instrument 100. Briefly, surgical instrument 100 includes a handle/actuator assembly 110 having a disposable loading unit 112 which is removably and rotatably attached to the handle/actuator assembly 110 by way of intermediate section 114 which extends from a distal end of housing/actuator assembly 110.

Figure 8:
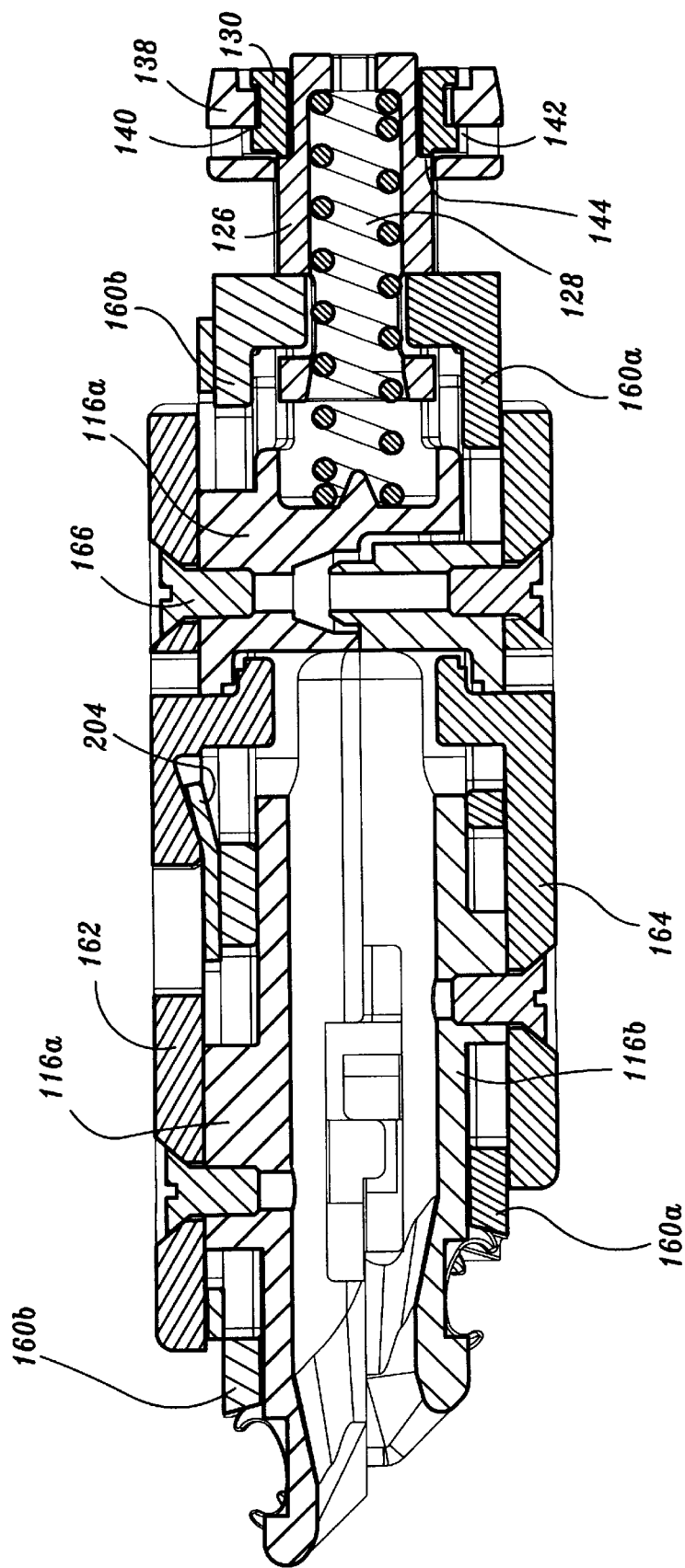
FIG. 8 is a horizontal cross-sectional view of the disposable loading unit shown greatly enlarged for clarity.
Figure 9:
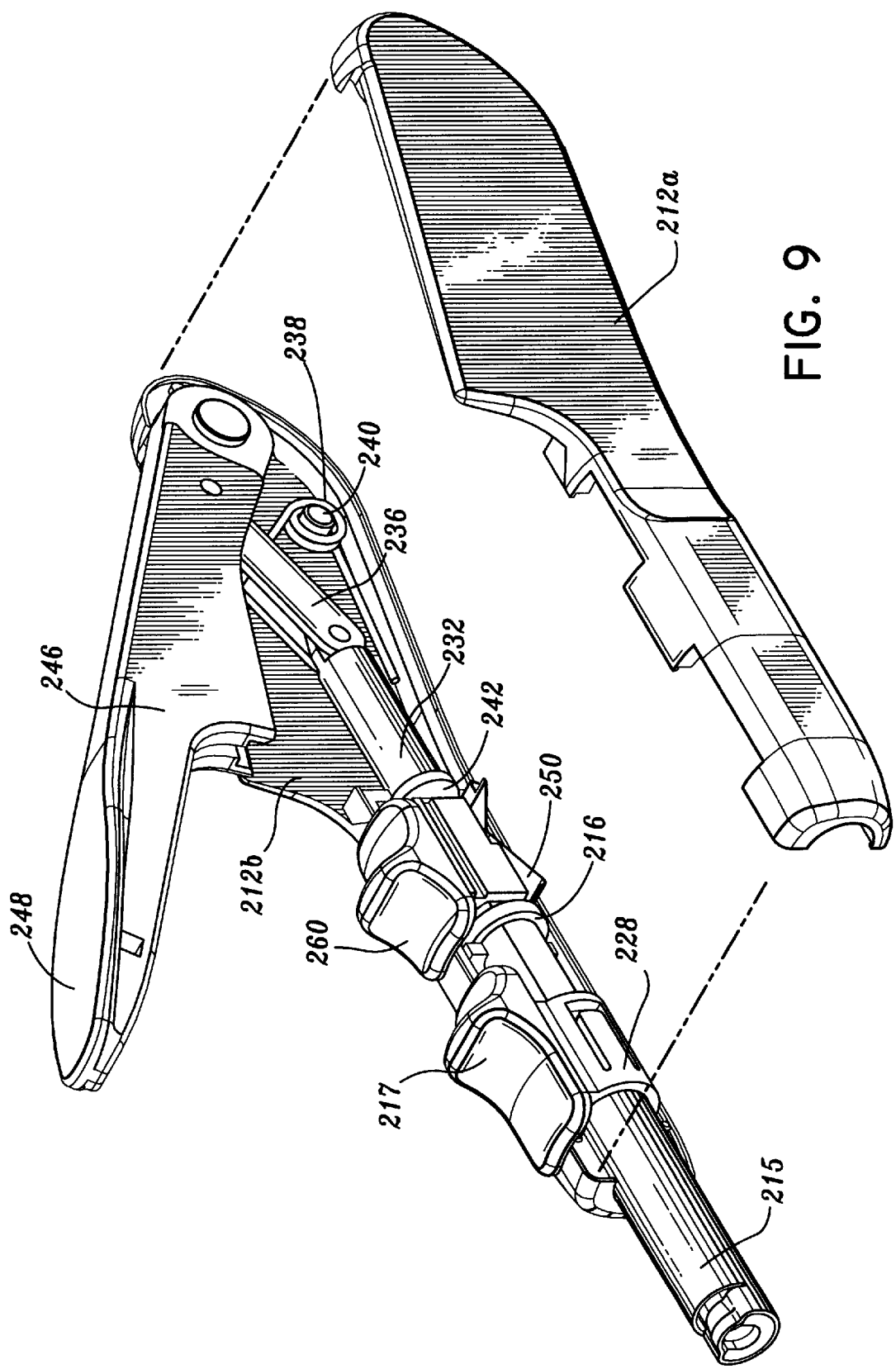
FIG. 9 is a perspective view of a handle/actuator assembly of the surgical instrument with parts separated.
Figure 12:
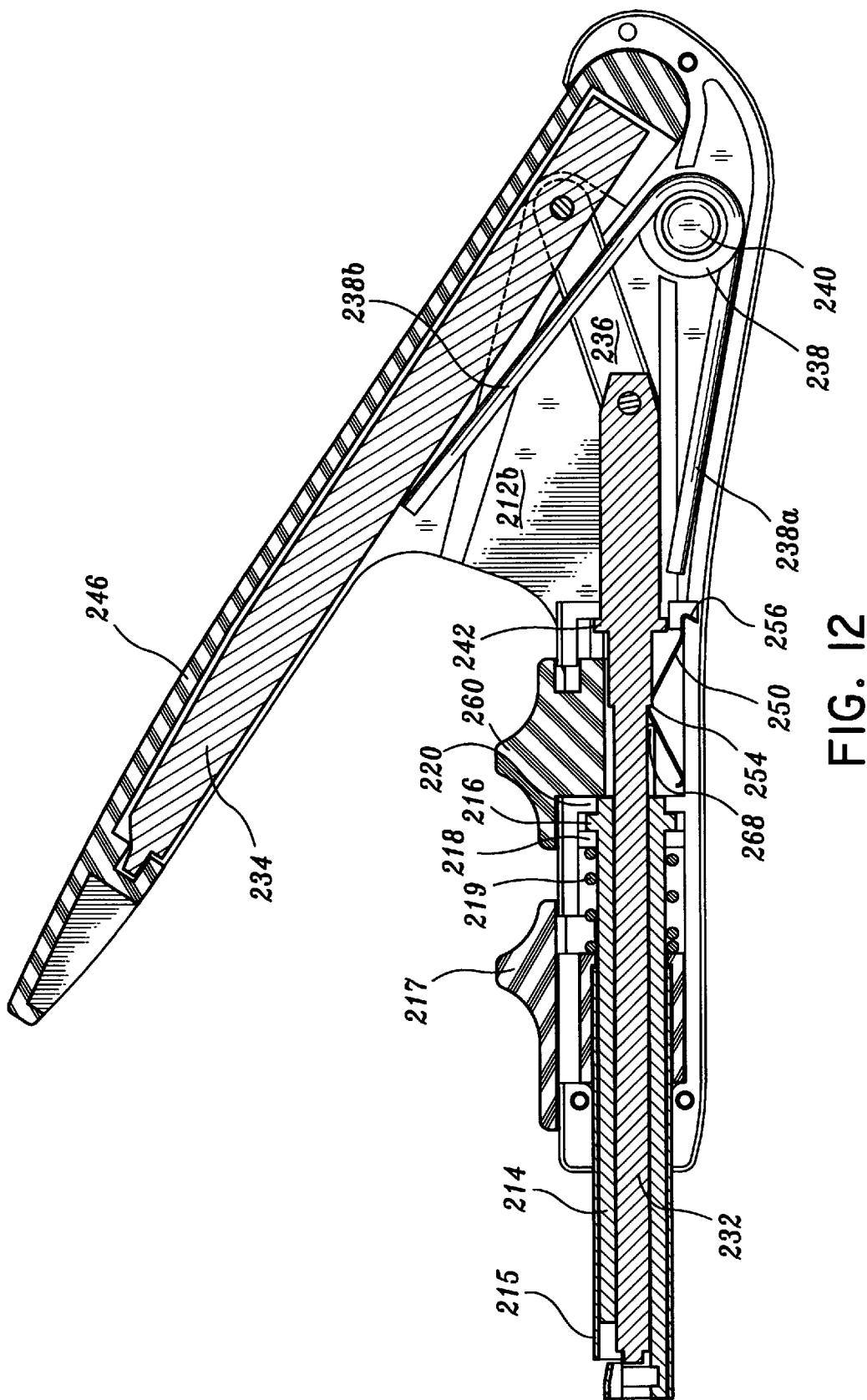
FIG. 12 is a horizontal cross section of the handle/actuator assembly.

Referring now to FIGS. 2–8, disposable loading unit 112 includes a two-part fastener support member made up of split half-sections 116a and 116b which form a hinge and are connected to each other by hinge pin 118. Split half-section 116a includes an actuator barrel 120 which forms a bore that opens at a proximal end. Actuator barrel 120 includes opposed longitudinal slots 122 and 124 to facilitate operation of an actuator member 126 which is slidably mounted in actuator barrel 120. Actuation member 126 is spring biased to a proximal-most orientation by a coil spring 128. Actuator 126 is further retained within actuator barrel 120 by a lock ring 130 which includes an annular groove 132 defined by proximal and distal flanges 134 and 136, respectively. Each of the proximal and distal flanges 134 and 136 include a pair of opposed slotted portions which are aligned to facilitate locking of ring 130 anterior portion of a mounting hub 138. For example, by way of passing lock ring 130 over opposed extended tabs 140 and 142, as best seen in FIG. 8, at the rotating lock ring 130 one quarter turn such that the pairs of opposed slots formed in proximal flange and distal flange 134 and 136, respectively, are rotated 90° with respect to tabs 140 and 142. Lock ring 130 is biased against the distal facing surfaces of extended tabs 140 and 142 by the force of compressed coil spring 128 which is disposed in the bore formed longitudinally within actuator 126. In particular, a shoulder portion 144 of actuator 126 is biased against an annular lip 146 (FIG. 4) which is formed on the distal facing surface of lock ring 130. Actuator member 126 further includes a pair of opposed transversely extending slots 148 and 150 formed on the outer surface thereof which, as will be described in further detail herein, provide an engagement surface for a fastener pusher member.

Split half-sections 116a and 116b of the fastener support member are provided with fastener retaining sections 152 and 154. Each of fastener retaining sections 152 and 154 are provided with a plurality of longitudinal channels 156 which are configured and dimensioned to support a "C"-shaped surgical fastener or clip 158 therein by, for example, friction or partial compression of clips 158. Fastener retaining sections 152 and 154 are preferably arranged such that longitudinal channels 156 form an eccentric array radially about the outer surface of fastener support member 116. This arrangement facilitates the efficacious formation of an angled connection or fistula between the vessels to be joined. Such a connection facilitates better fluid flow through the anastomotic site.

A fastener pusher member 160 is provided to facilitate deformation of clips 158 during firing of the instrument. Fastener pusher member 160 is made up of split half-sections 160a and 160b which are secured to split half-sections 116a and 116b, respectively, by way of mounting plates 162 and 164 and screws 166 which are threaded into threaded holes formed in receiving posts 168, 170; and 172, 174 disposed on split half-sections 116a and 116b, respectively. Mounting plates 162 and 164 are attached to split half-sections 116a and 116b in a manner to permit longitudinal sliding movement of split half-sections 160a and 160b of fastener pusher member 160 relative to fastener support member 116. This sliding movement is facilitated by longitudinally aligned slots 176, 178; and 180, 182 which are provided on split half-sections 160a and 160b, respectively.

Split half-sections 160a and 160b are further provided with molded surfaces such as protrusions 184 and depressions 186 as shown on split half-section 160a which interfit with corresponding protrusions and depressions formed on split half-section 160a so as to prevent relative longitudinal movement of split half-sections 160a and 160b. Stepped camming or pusher surfaces 188 are formed on the distal ends of each of split half-sections 160a and 160b and serve to cam a proximally oriented portion of clips 158 towards a distal oriented portion of clips 158. This motion effects deformation of the clips upon firing of surgical instrument 100.

Finally, a hinge lock 190 is mounted between mounting plate 162 and split half-section 160b. Hinge lock 190 is provided with latch portions 192 and 194 which extend transversely across one side of disposable loading unit 112 to latch onto raised correspondingly shaped surfaces 196 and 198, respectively, formed on the outer surface of split half-section 160a. Hinge lock 190 is further provided with a pair of longitudinally oriented slots 200 and 202 which are radially aligned with slots 180 and 182 of split half-section 160b to facilitate relative longitudinal movement of hinge lock 190 with respect to both split half-section 160b and split half-section 116a. A flexible return lockout tab 204 extends proximally from the distal end of slot 202 and is cantilevered outwardly away from a plane defined by slots 202 and 204 such that it is positioned in a tab receiving recess 206 formed on the inner surface of mounting plate 162 when the DLU 112 is in a pre-fired condition. A lockout slot 208 is formed longitudinally aligned with tab receiving recess 206 and spaced distally therefrom such that upon distal movement of hinge lock 190 (when split half-section 160b is moved distally), return lockout tab will be deflected to a flattened condition and will extend into lockout slot 208 in order to prevent subsequent proximal movement of hinge lock upon proximal movement of split half-section 160b after firing of surgical instrument 100.

In this manner, after firing of surgical instrument 100, latch portions 192 and 194 of hinge lock 190 will remain distal relative to raised surfaces 196 and 198 of split half-section of 160a by permitting the split half-sectioned DLU 112 to be opened by pivoting split half-sections 116b and 160a away from split half-sections 116a and 160b to facilitate removal of the vessel segment from within the vessel pathway formed through the distal end of DLU 112 and out through a lateral opening 210 formed by aligned molded recesses formed in each of split half-sections 116a, 116b; and 160a and 160b of fastener support member 116 and fastener pusher member 160, respectively.

Referring now to FIGS. 9–12, the handle/actuator assembly 110 of surgical instrument 100 will now be described in detail. Handle/actuator assembly 110 includes a housing formed of half-sections 212a and 212b which are preferably molded to have recessed inner surfaces and contours formed therein to house the various components which are contained within handle/actuator assembly 110. In particular, handle/actuator assembly 110 includes a DLU mounting assembly which facilitates detachable mounting of a DLU 112 to the distal end of handle/actuator assembly 110. The DLU mounting assembly includes an elongated holding tube 214 which is held longitudinally and rotationally fixed relative to housing half-sections 212a and 212b. This mounting arrangement may be accomplished for example, by way of an annular flange 216 formed adjacent the proximal end of holding tube 214 being held within an annular groove defined by partition wall segments 218 and 220 formed in each of housing half-sections 212a and 212b. Holding tube 214 is further prevented from rotational movement by way of flattened sidewall portions 222 formed on opposing sides of holding tube 214 being retained within and abutting flat surfaces 224 and 226 formed long partition wall segments 218 and 220, respectively, in each of housing half-sections 212a and 212b. DLU locking tube 215 is secured within a collar 228 formed on slide 217. Tube 215 may be secured in slide 217 by any suitable means, for example, friction fitting bonding, adhesives, or the like. Coil spring 219 is interposed in housing half-sections 212a and 212b between partitioned segments 218 and the proximal end surface of collar 228. In this manner, locking tube 215 is biased in a distal-most position which corresponds to a locked position to retain DLU 112 on the distal end of surgical instrument 100. The distal end of DLU holding tube 214 is provided with a semi-annular groove 230 which is dimensioned to receive mounting hub 138 formed at the proximal end of DLU 112. Semi-annular groove 230 is dimensioned to permit DLU mounting hub 138 to rotate within the groove.

Handle and actuator assembly 110 further includes a firing assembly which facilitates movement of actuator 126 housed within the actuator barrel 120. In the embodiment illustrated in FIGS. 9–15, the firing assembly is a linkage mechanism which imparts reciprocating longitudinal movement in an actuator rod by way of movement of an actuator lever. However, it is within the scope of the present disclosure that the actuator rod may be reciprocatingly moved by any suitable known methods. The firing assembly basically includes an actuator rod 232 which is connected to an actuator lever 234 by way of links 236 pivotally attached at either end to actuator rod 232 and actuator lever 234, respectively. Actuator rod 232 is slidably disposed within a longitudinal bore formed through DLU holding tube 214. Actuator rod 232 is biased in a proximal-most position by way of a torsion spring 238 being mounted on a post 240 formed near the proximal end of housing half-section 212b. Extended legs 238a and 238b are provided on torsion spring 238 to bias actuator lever 234 upwardly away from housing half-sections 212a and 212b thereby pulling actuator rod 232 toward its proximal-most position as determined by the abutment of annular shoulder 242 against partition 244 formed in each of housing half-sections 212a and 212b. To facilitate comfort and ease of operation for the user, a cover 246 is secured over actuator lever 234 and is independently pivotally mounted to housing half-sections 212a and 212b. Cover 246 is provided with an ergonomic surface 248 which is contoured and configured to be comfortably actuated by the thumb of a user when handle and actuator assembly 210 is held in the palm of the user's hand.

A firing safety mechanism is also provided to prevent premature firing of surgical instrument 100. In the illustrated embodiment, the firing safety assembly includes an inverted leaf spring 250 having a cut-out portion 252 formed therein which biases against a shoulder 254 formed on actuator rod 232. Spring 250 is further provided with a hook portion 256 formed at the proximal end thereof which latches onto a protruding surface 258 formed in housing half-sections 212a and 212b. In this manner, spring 250 prevents distal movement of actuator rod 232 when the safety mechanism is armed. A safety release slide 260 which includes an upwardly extending contact surface which is exposed from the upper surface of housing half-sections 212a and 212b to permit the user to operate the slide and forms a clevis on a lower portion thereof which receives a flattened section 266 of actuator rod 332. Safety release slide 260 is further provided with a camming surface 268 along the lower edge thereof which cams the spring 250 out of contact with shoulder 254 upon proximal movement of safety release slide 260.

In use, as shown in FIGS. 13–31, surgical instrument 100 facilitates the performance of a vascular anastomosis without the need for manual suturing of the vessels. The method and usage described herein will be addressed in terms of minimally invasive vascular anastomosis performed on a beating heart such as in a MIDCAB procedure. However, the presently disclosed surgical instrument may also be used in performing anastomoses of other tubular or luminal body structures without departing from the scope of the present disclosure. For example, surgical instrument 100 may be used in conventional open CABG procedures using a median sternotomy or other large incision without stopping the heart. Alternatively, the thoracic "window" procedure may be used to achieve access to the heart. The "window" approach involves a smaller incision and less displacement of the ribs, and therefore is less traumatic to the patient. For this approach, conventional surgical techniques are used to determine the location of the incision to access the chest cavity.

Figure 13:
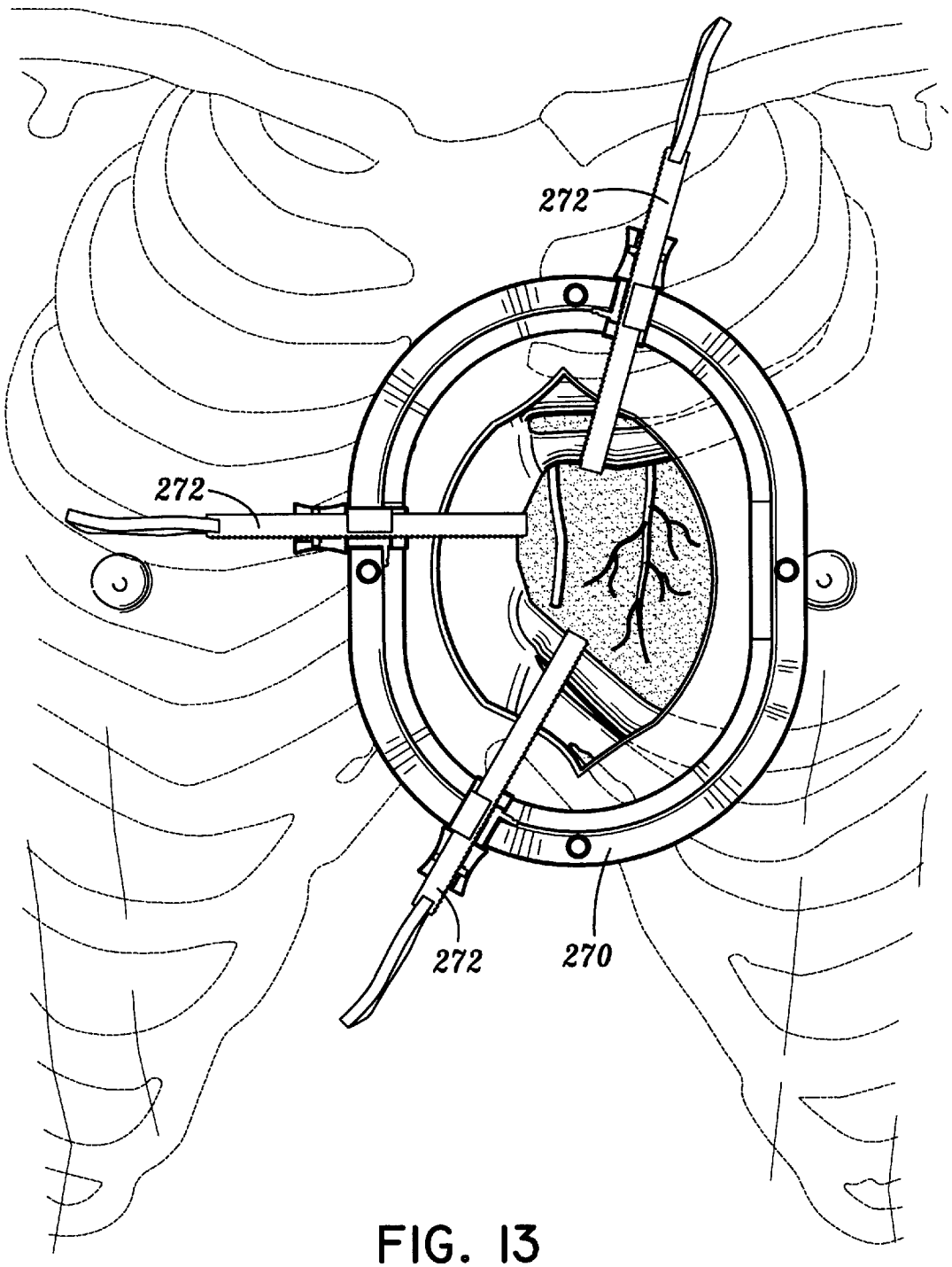
FIG. 13 is a view showing an operating "window" with the patient's heart exposed.

In particular, a surgical retractor assembly may be used to separate the ribs at the site of the incision as shown in FIG. 13. Specifically, a base 270 is placed on the chest of the patient with the central opening defined by the base being positioned over the operative site. Retractor assemblies 272 are mounted to the base at various locations. Each of retractor assemblies 272 includes a blade having a hook to engage either a rib or the sternum therewith. The retractor assemblies are mounted and used to retract ribs until a sufficiently large opening in the chest cavity is defined to provide direct access to the heart. For example, the sternum and the fourth and fifth ribs can be split apart to create a window. Other configurations of spreading the ribs and/or selectively cutting individual ribs away from the sternum may also be utilized for a particular procedure. Once the desired access to the heart is achieved, the graft vessel, e.g., the internal memory artery (IMA) is dissected from the surrounding cartilage and muscle, in a free end of the vessel is exposed. The occluded coronary artery, e.g., the left anterior descending artery (LAD), is then prepared for receiving the IMA graft. The heart is positioned in the desired orientation either by traction sutures passing through the pericardium or by manipulation with heart manipulation instruments which are held by the surgical personnel or clamped in a fixed orientation to a base such as the retractor assembly base. One such heart manipulating instrument is available from United States Surgical Corporation of Norwalk, Connecticut. Blood flow through the LAD can be restricted by cardiopulmonary bypass and pericardial cooling. Alternatively, a damping instrument may be applied directly on the LAD to restrict blood flow and reduce movement of the heart near the LAD. Such a heart stabilizing instrument is also available from United States Surgical Corporation of Norwalk, Connecticut.

Figure 14:
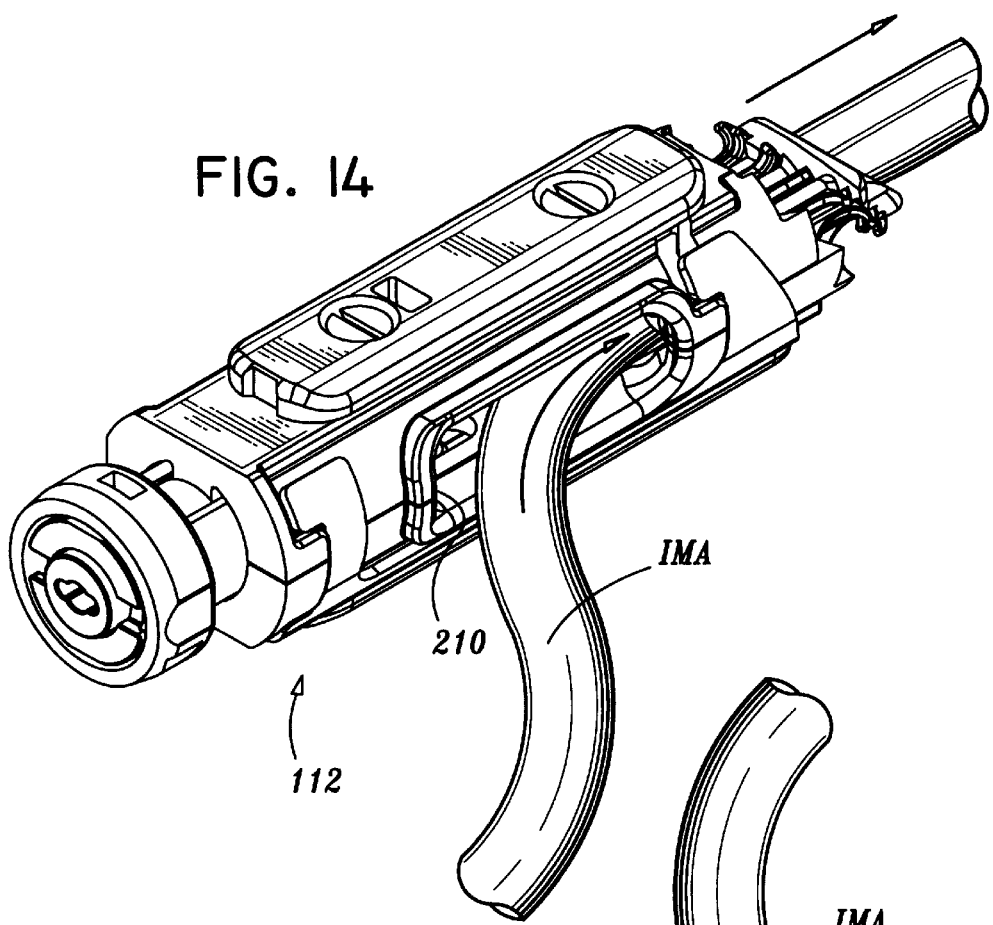
FIG. 14 is a perspective view of a disposable loading unit with a first vessel inserted therethrough.
Figure 15:
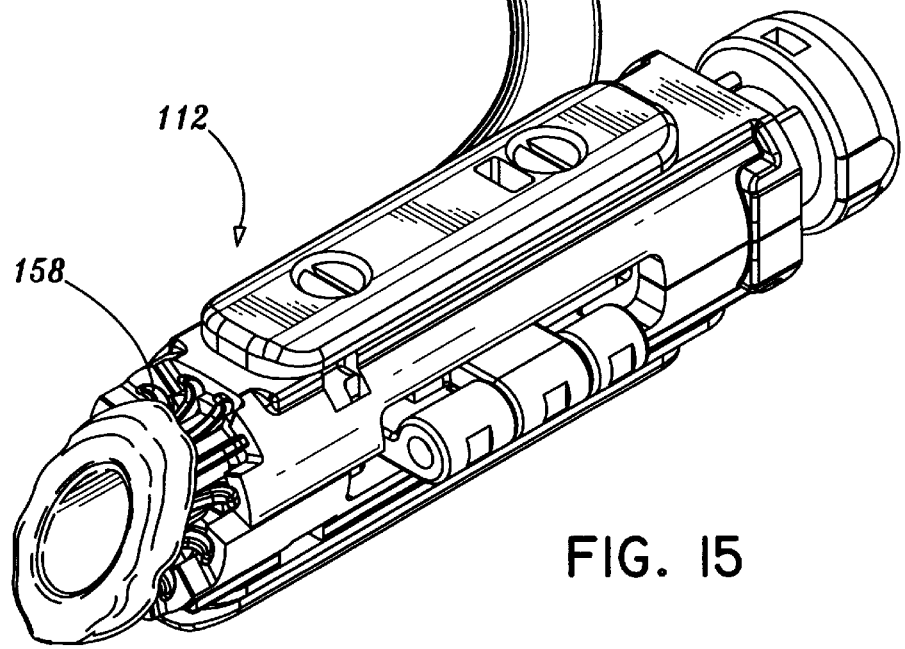
FIG. 15 is a perspective view of the disposable loading unit shown in reverse angle from that of FIG. 14, which shows the vascular tissue everted over a plurality of surgical fasteners.
Figure 16:
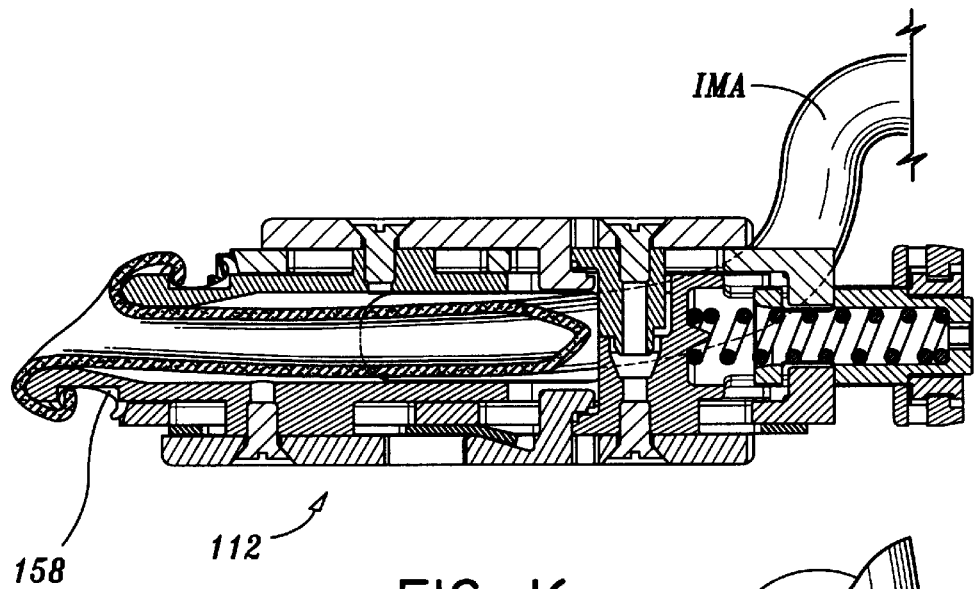
FIG. 16 is a horizontal cross-sectional view of the disposable loading unit of FIG. 15.
Figure 17:
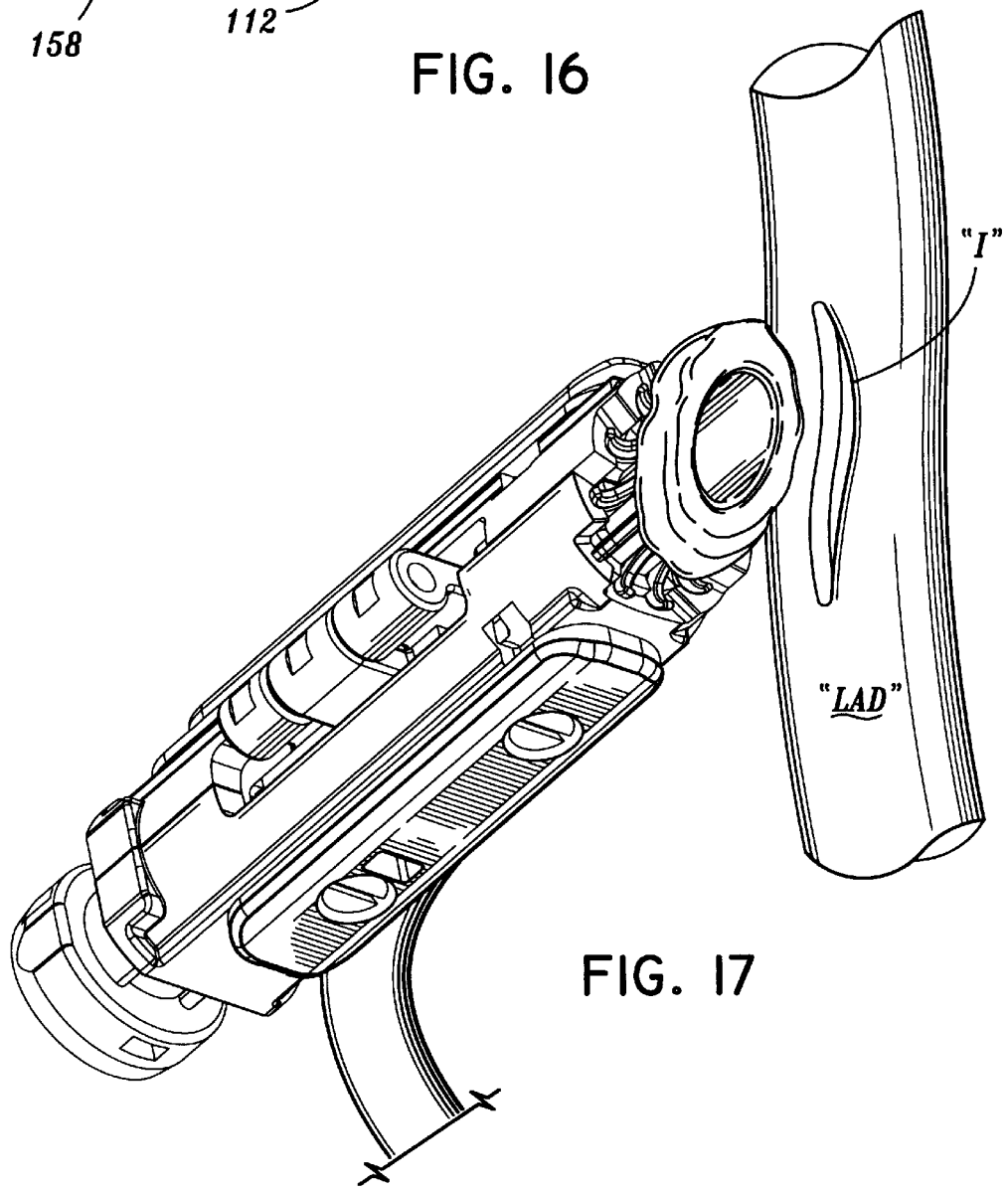
FIG. 17 is a perspective view showing insertion of the disposable loading unit and everted vascular tissue through a second vessel.
Figure 18:
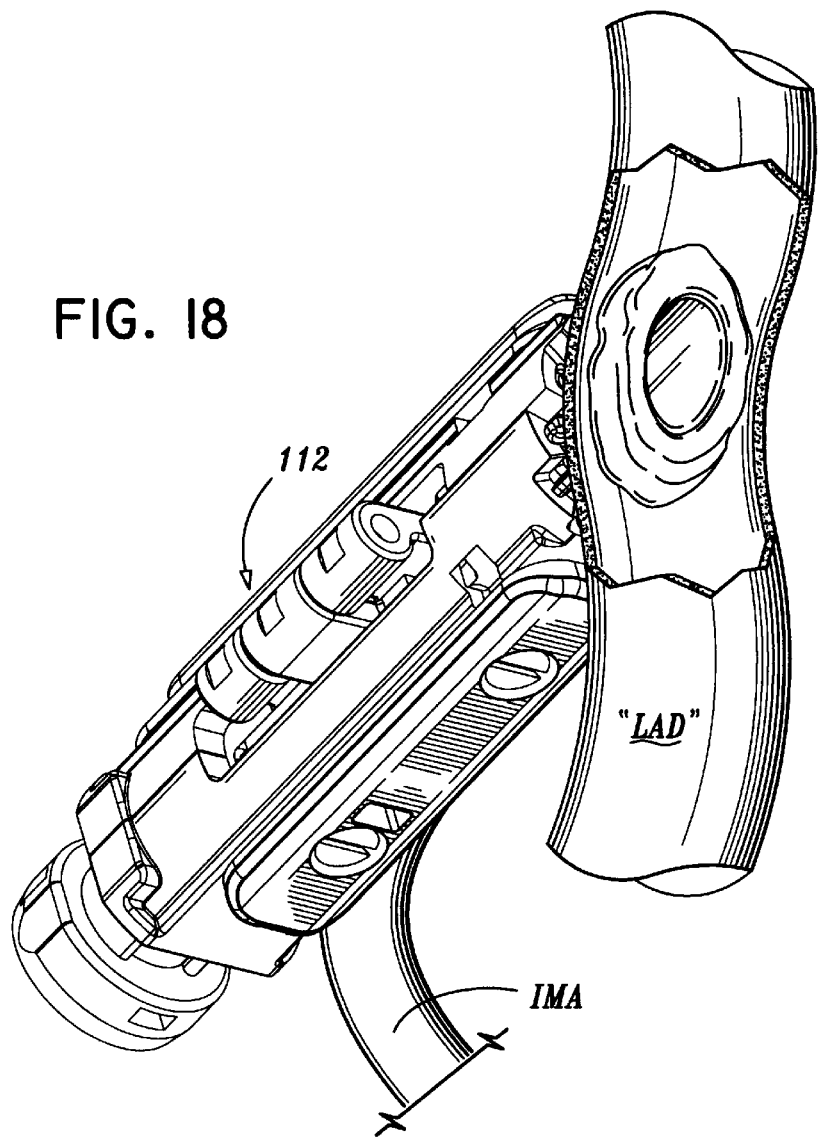
FIG. 18 is a view similar to FIG. 17, which shows full insertion of the distal end of the disposable loading unit with the everted vascular tissue through an incision formed in the second vessel.
Figure 19:
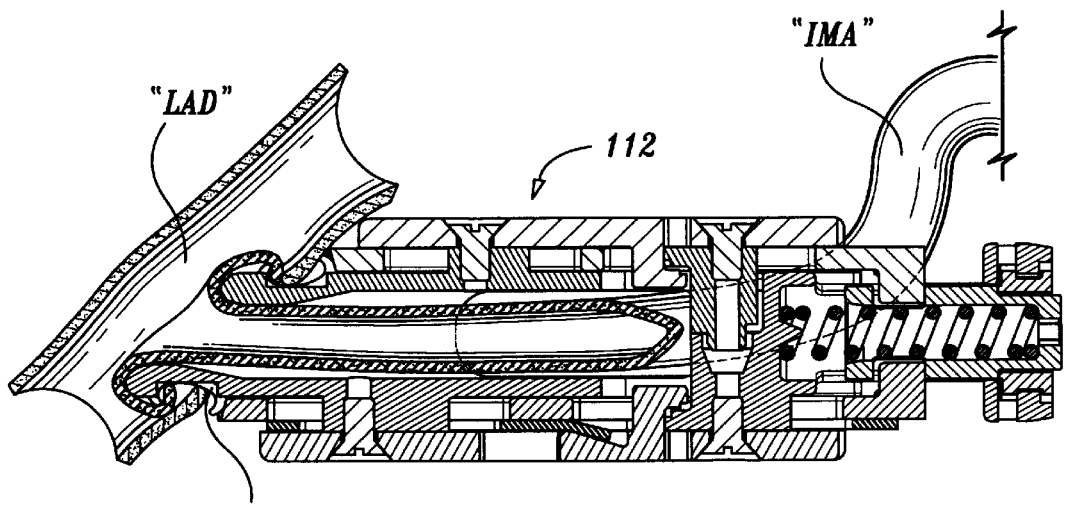
FIG. 19 is a horizontal cross-sectional view of the inserted disposable loading unit of FIG. 18.

Referring to FIG. 14, the free end of the IMA is inserted through lateral opening 210 of DLU 112 and passed out the distal end opening of the DLU. The free end of the IMA is then everted over the distal end of the DLU such that the end of the IMA is retained by the distal end oriented portions of clips 158 as best shown in FIG. 15 and FIG. 16. Everting of the tissue may be achieved by any suitable known techniques such as y using graspers. With the IMA loaded in DLU 112, the DLU is manipulated preferably detached from the handle and actuator assembly 110 in approximation to an incision "I" formed in the LAD, as shown in FIG. 17. Referring to FIGS. 18 and 19, the DLU with the everted IMA is inserted into the incision "I" of the LAD such that the walls of the LAD surrounding the incision are retained between the everted end of the IMA and the proximal ends of clips 158, as shown in FIG. 19. As previously noted, the distal end of DLU 112 is configured with an angle relative to a transverse plane of the DLU in order to optimize the anastomosis and to facilitate optimal blood flow across the graft site from the IMA to the LAD. This junction creates "heel" and "toe" portions in which an acute or obtuse angle between the vessels is defined.

Once DLU 112 with the everted IMA has been successfully inserted through the incision of the LAD, the surgeon may then attach the handle/actuator assembly 110 to DLU 112 as shown in FIGS. 20 and 21. In particular, the DLU lock slide 217 is moved proximally as indicated by arrow "A" in order to retract locking tube 215 and thereby expose the distal end of DLU holding tube 214, and in particular, semiannular groove 230. DLU 112 is inserted on the distal end of the handle and actuator assembly 110 by placing mounting hub 138 within semi-annular groove 230 and releasing the force applied on DLU lock slide 217 as indicated by arrow "B" in FIG. 21, to permit coil spring 219 to return lock slide 217 and locking tube 215 to their distal-most orientations thereby securing the DLU in place.

Figure 22:
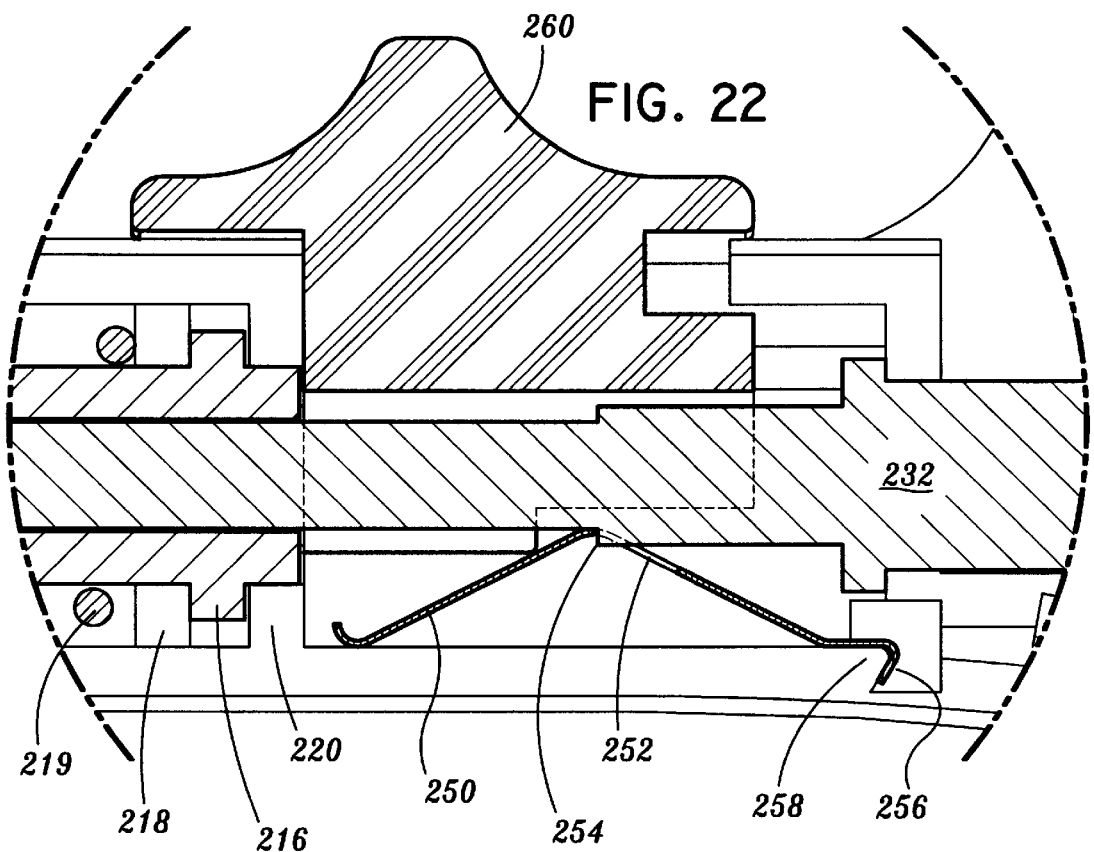
FIG. 22 is an enlarged view isolating on the safety firing lockout member of the handle/actuator assembly.
Figure 23:
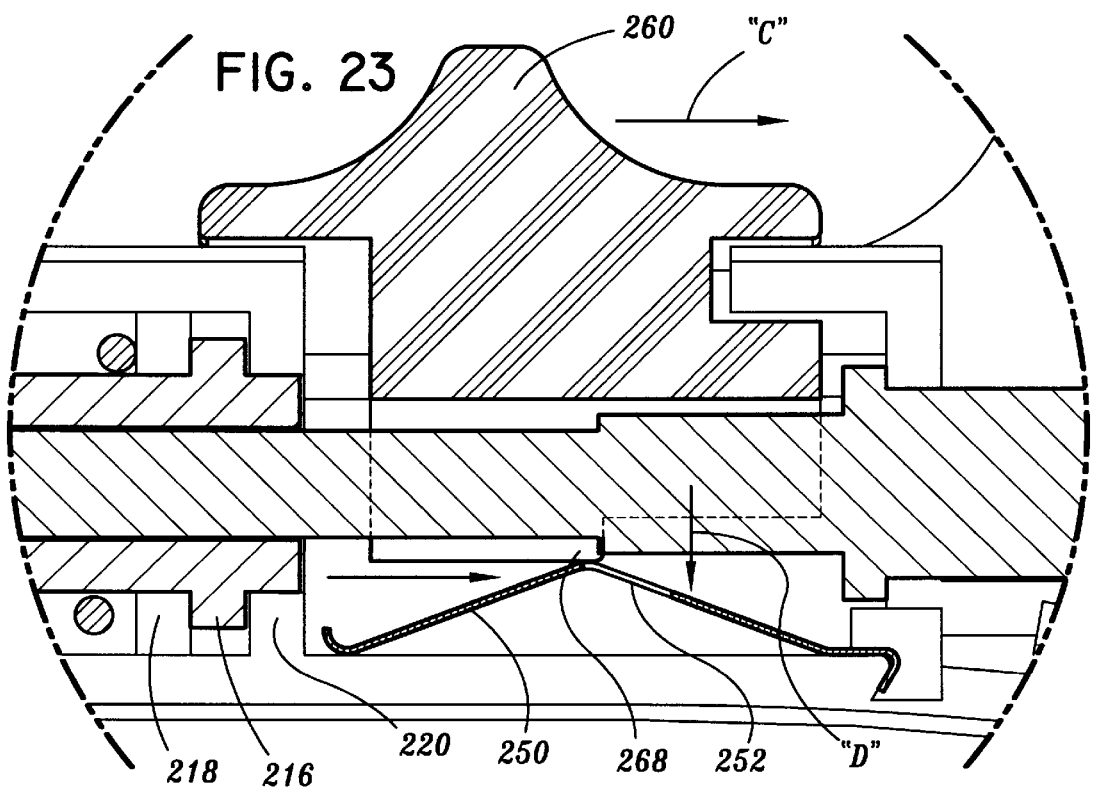
FIG. 23 is a view similar to FIG. 22, which shows operation of the safety firing lockout.
Figure 25:
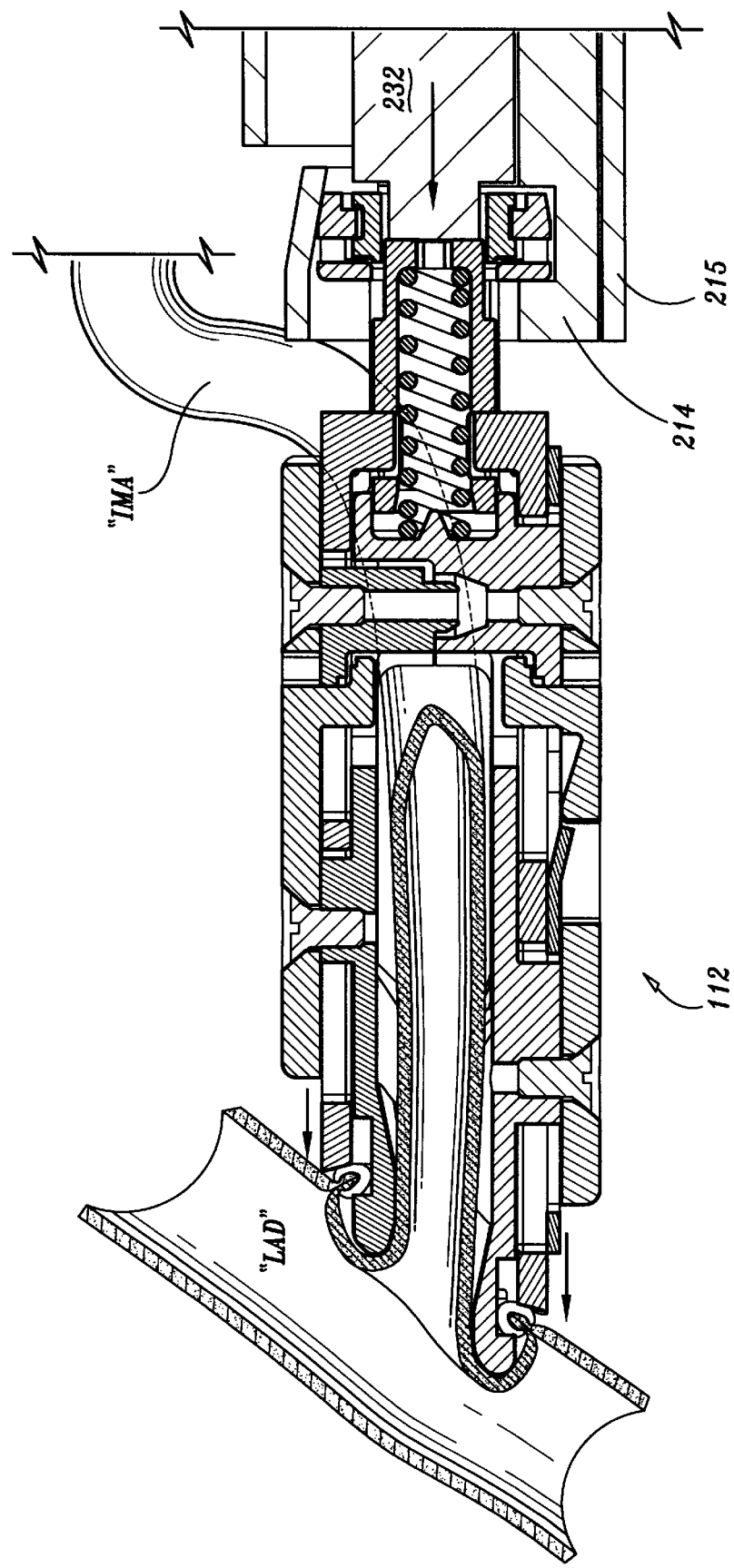
FIG. 25 is an enlarged horizontal cross-sectional view of the distal end of the handle/actuator assembly and the disposable loading unit, which shows the deformation of the surgical fasteners.
Figure 26:
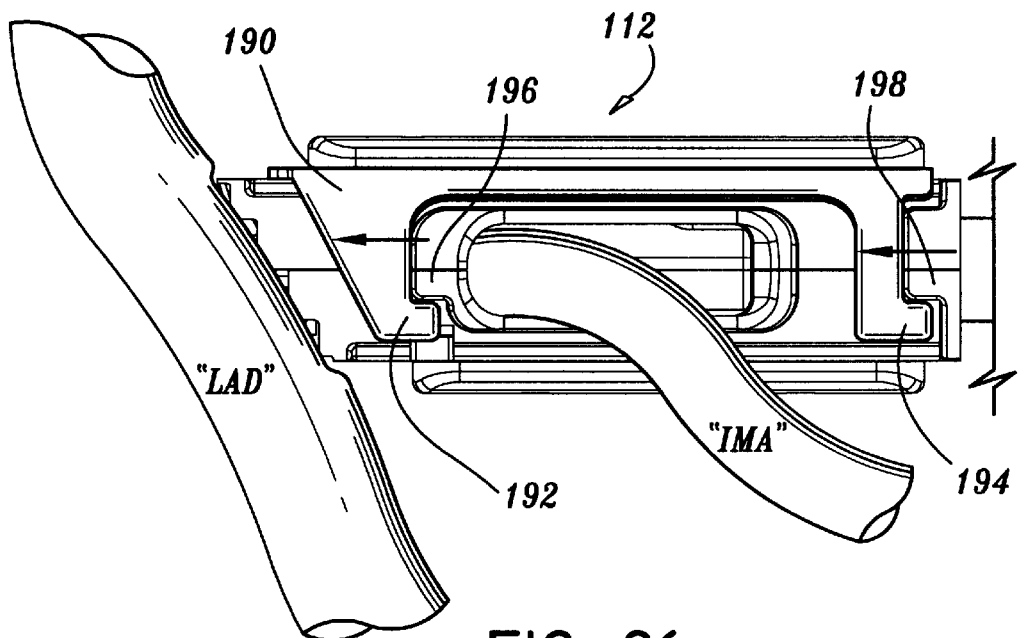
FIG. 26 is a side view showing operation of the disposable loading unit.
Figure 27:
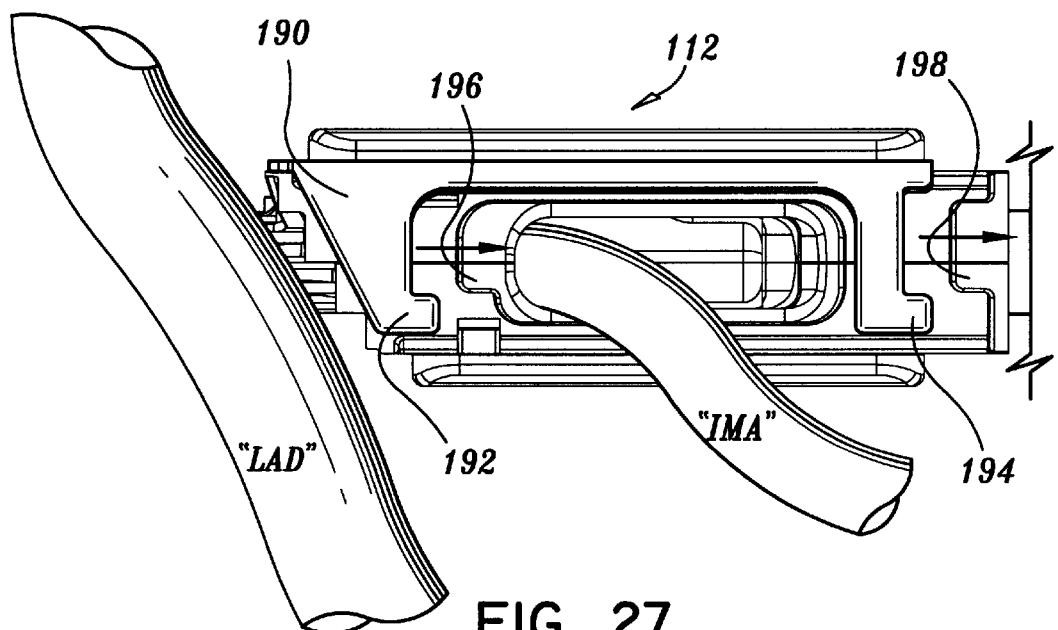
FIG. 27 is a view similar to FIG. 26, which shows retraction of a pusher member of the disposable loading unit after deformation of the surgical fasteners.

Referring to FIGS. 22 and 23, when the surgeon is ready to complete the anastomosis, the safety release slide 260 is moved proximally as indicated by arrow "C" in FIG. 23 thereby causing camming surface 268 to cam spring 250 downwardly away from shoulder 254 as indicated by arrow "D". Thereafter, the surgeon may depress cover 246 towards handle half-sections 212a and 212b, as indicated by arrow "E" in FIG. 24, causing actuator rod 232 to drive actuator 126 of DLU 112 distally as indicated by arrow "F", thereby moving pusher member split half-sections 160 and 160b distally to deform clips 158 as shown in FIGS. 25 and 26.

Figure 24:
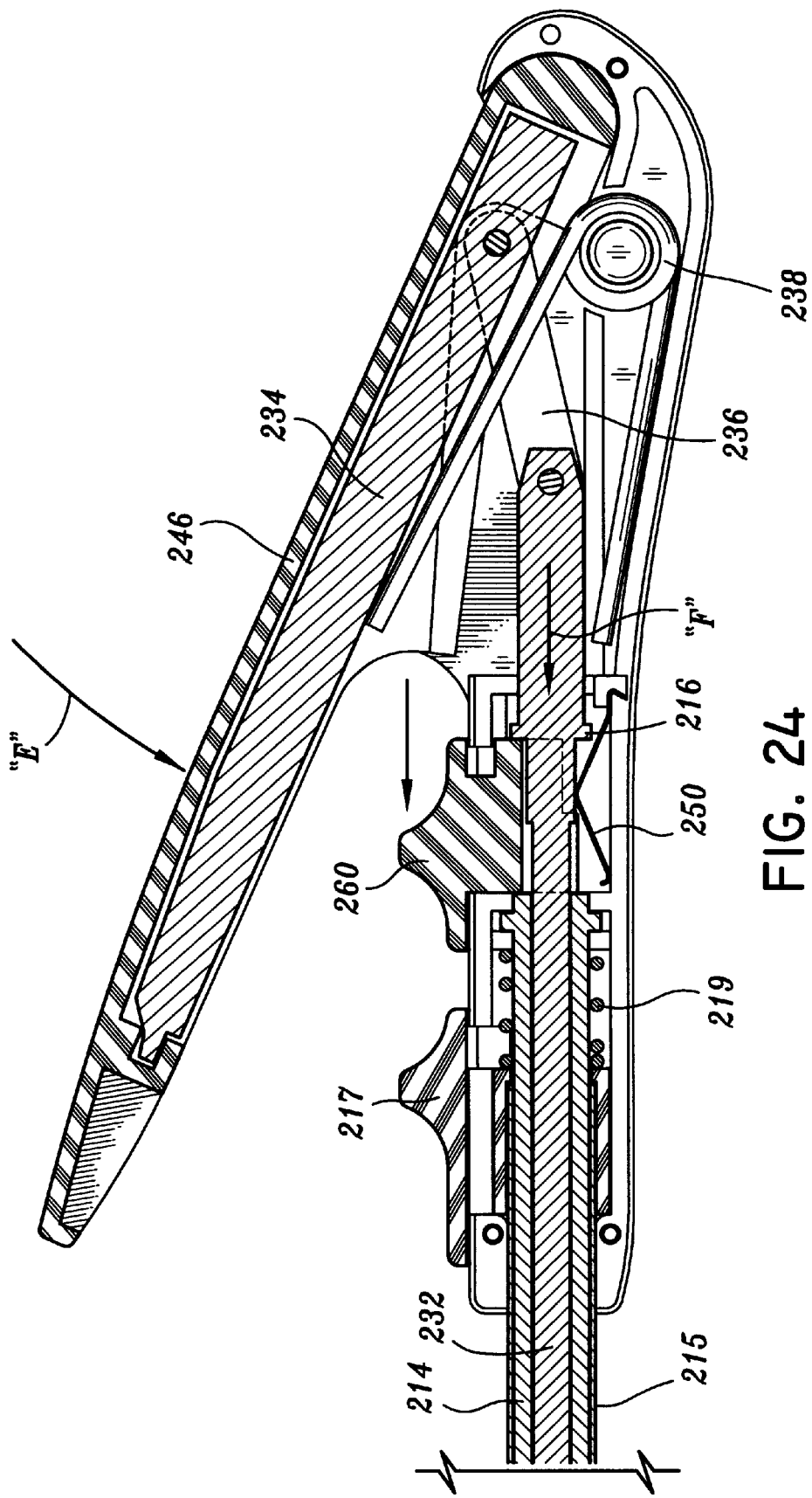
FIG. 24 is a horizontal cross-sectional view of the handle/actuator assembly, which shows the firing sequence of the handle/actuator assembly.

As best illustrated in FIG. 24, one particularly advantageous feature of the presently disclosed surgical instrument is that upon actuation of handle/actuator assembly 110, safety release slide 260 is urged back into its initial locked orientation by way of annular flange 216 of actuator rod 232 pushing the lower portion of safety release slide 260 during the distal movement of actuator rod 232. In this manner, upon release of cover handle 246, the potential energy created by the compression of torsion spring 238 will cause actuator rod 232 to be pulled back proximally thereby engaging shoulder 254 with cutout 252 of spring 250. This will serve to prevent accidental re-firing action of surgical instrument 100.

Referring to FIGS. 26–30, a farther uniquely advantageous feature of surgical instrument 100 is hinge lock 190 and its operation. Upon firing of surgical instrument 100, return lockout tab 204 of hinge lock 190, which extended into lockout slot 208 during distal movement of hinge lock 190 with split half-sections 160 and 160b, serves to retain hinge lock 190 distal of its original seated location in tab receiving recess 206. By retaining hinge lock 190 at this position, latch portions 192 and 194 are released from raised surfaces 196 and 198 of split half-section 160a of the pusher member. In this manner, split half-section 116b and 160a may be pivoted away from split half-sections 116a and 160b as shown in FIG. 30 to permit the removal of the IMA from within the pathway of the DLU thereby completing the vascular anastomosis as shown in FIG. 31.

Figure 31:
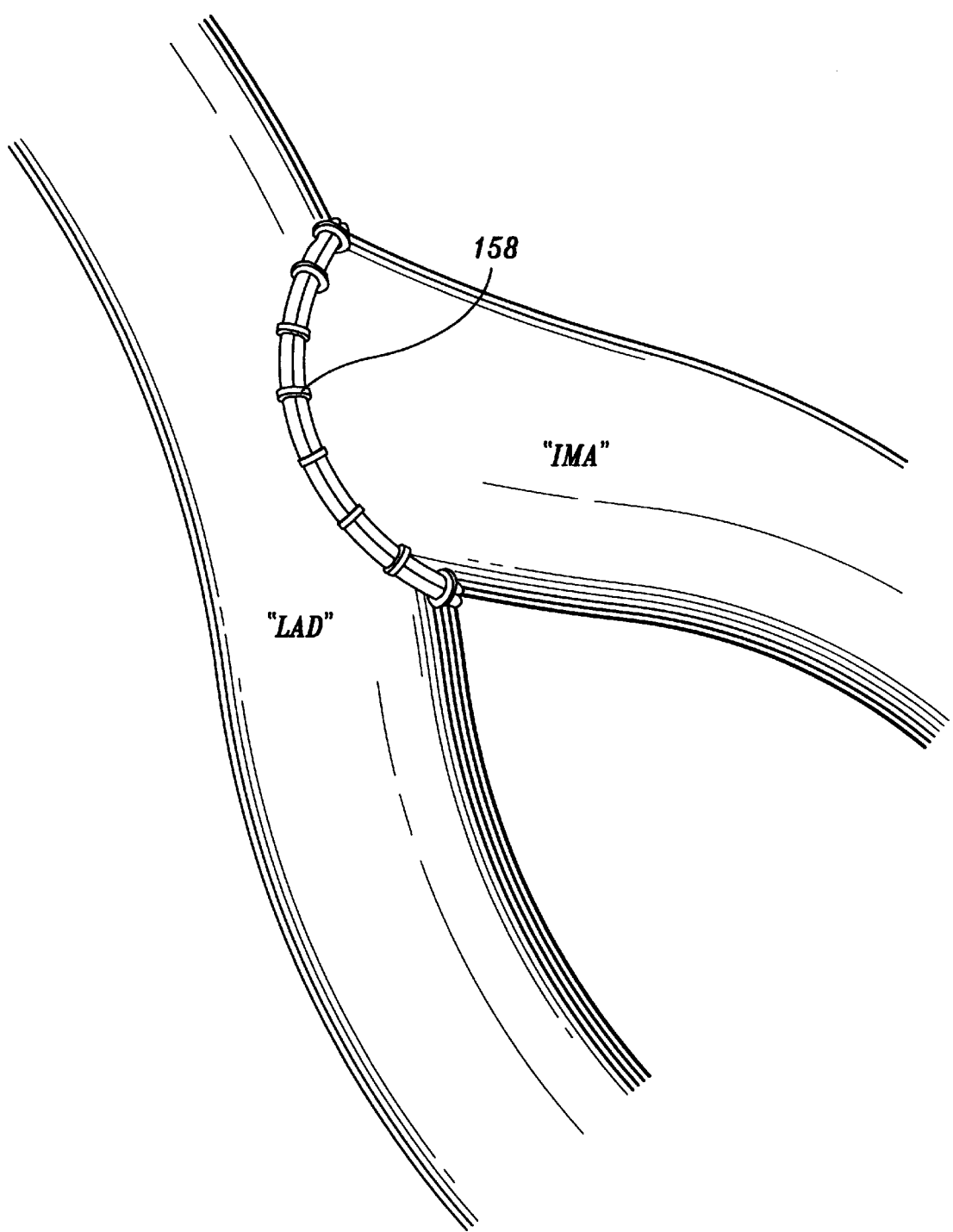
FIG. 31 is a view showing the completed anastomosis.
Figure 31A:
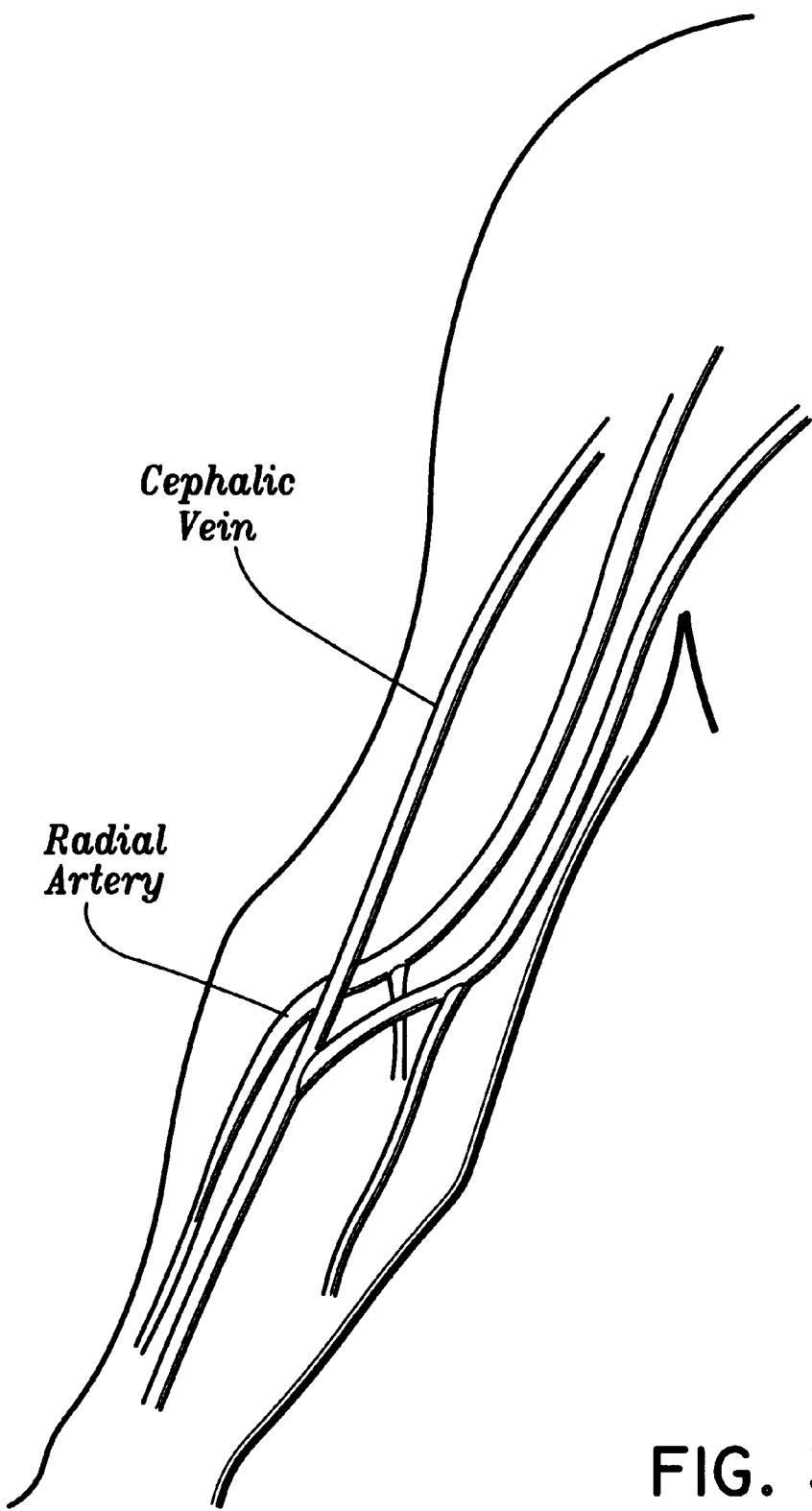
FIG. 31A is a view showing an alternative anastomosis site for a procedure known as an A-V fistula.
Figure 32:
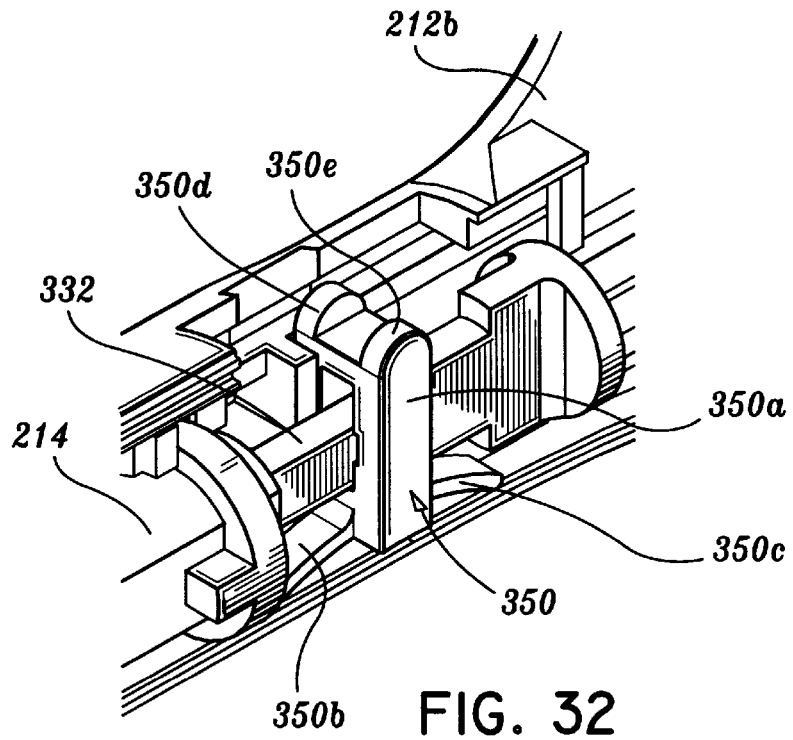
FIG. 32 is a perspective view of an alternative embodiment of a safety firing lockout member of the handle/actuator assembly.

Referring to FIG. 31 A, a portion of the vascular anatomy of an arm which may be an alternative utilized anastomosis site as illustrated wherein instead of joining the IMA to the LAD in a bypass procedure, an A-V fistula is performed utilizing surgical instrument 100 to join the radial artery end-to-side with the cephalic vein (sometimes called the radial vein). Other A-V fistulas which may also be achieved utilizing surgical instrument 100 include joining the ulnar artery end-to-side with the basilic vein (sometimes called the ulnar vein). Such A-V fistulas are performed to facilitate hemodialysis for end stage kidney disease to allow a single puncture at the dialysis unit for blood cleansing. The fistula allows a greater flow rate through the dialyzer (not shown).

Figure 33:
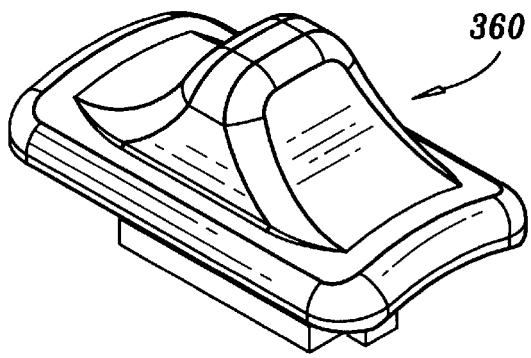
FIG. 33 is a perspective view of a safety release slide of the embodiment of FIG. 32.
Figure 33A:
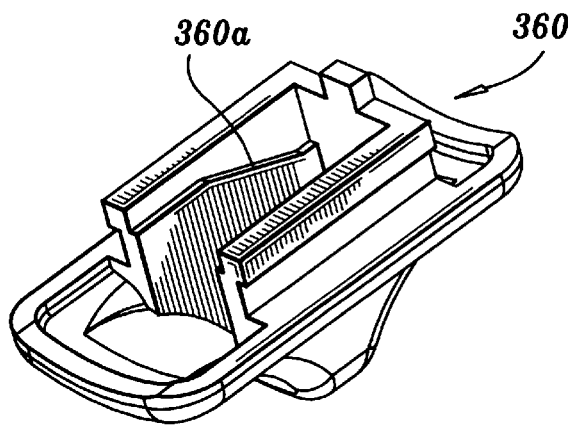
FIG. 33A is a perspective view showing the bottom of the safety release slide of FIG. 33.
Figure 34:
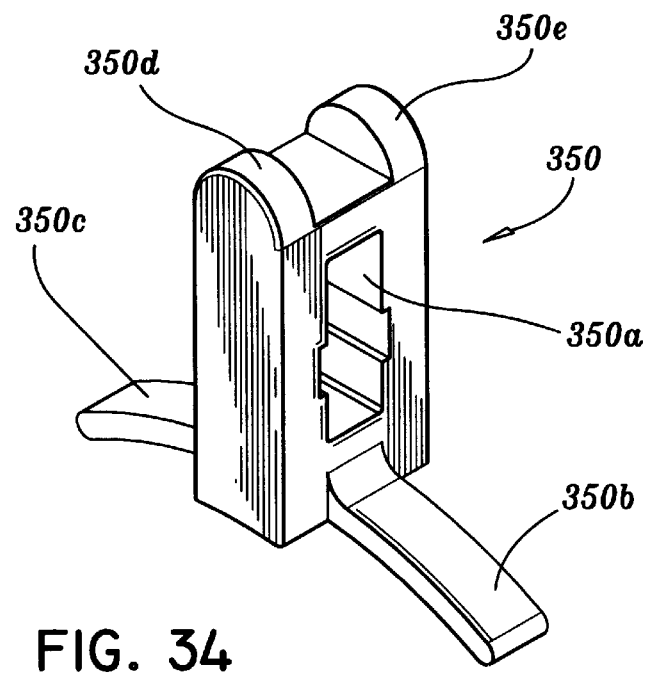
FIG. 34 is a perspective view of a lockout spring of the safety firing lockout of FIG. 32.
Figure 35:
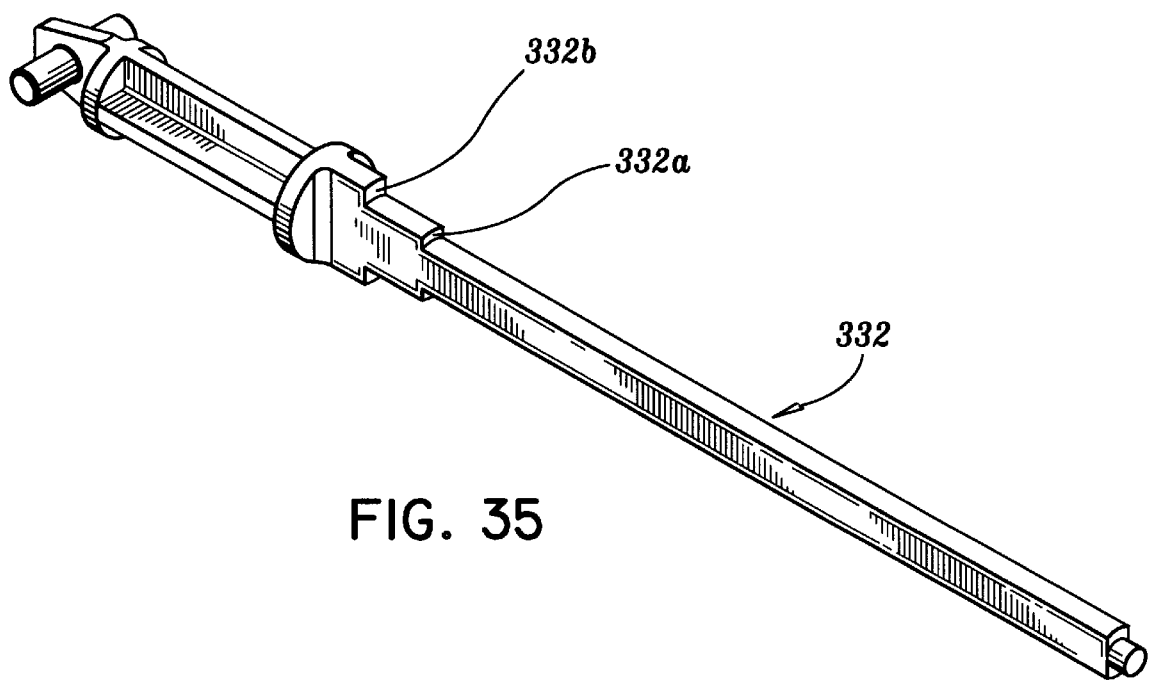
FIG. 35 is a perspective view of an actuator rod of the embodiment of FIG. 32.

Referring to FIGS. 32–39, an alternative embodiment of the firing safety mechanism illustrated in FIGS. 22–24 is illustrated which also prevents the unintended firing of surgical instrument 100. The firing safety mechanism includes a lock spring 350 and a safety release slide 360. Referring to FIGS. 33 and 33A, safety release slide 360 includes a pair of camming surfaces 360a and 360b which interact with cam follower surfaces 350d and 350e. Lock spring 350, as best illustrated in FIG. 34, includes a body portion 350a that defines a yoke, a pair a leaf spring portions 350b and 350c, and a pair of cam follower surfaces 350d and 350e formed along a top portion thereof. An actuator rod 332, FIG. 35, is configured and dimensioned to pass through yoke portion 350a of lock spring 350.

Figure 36:
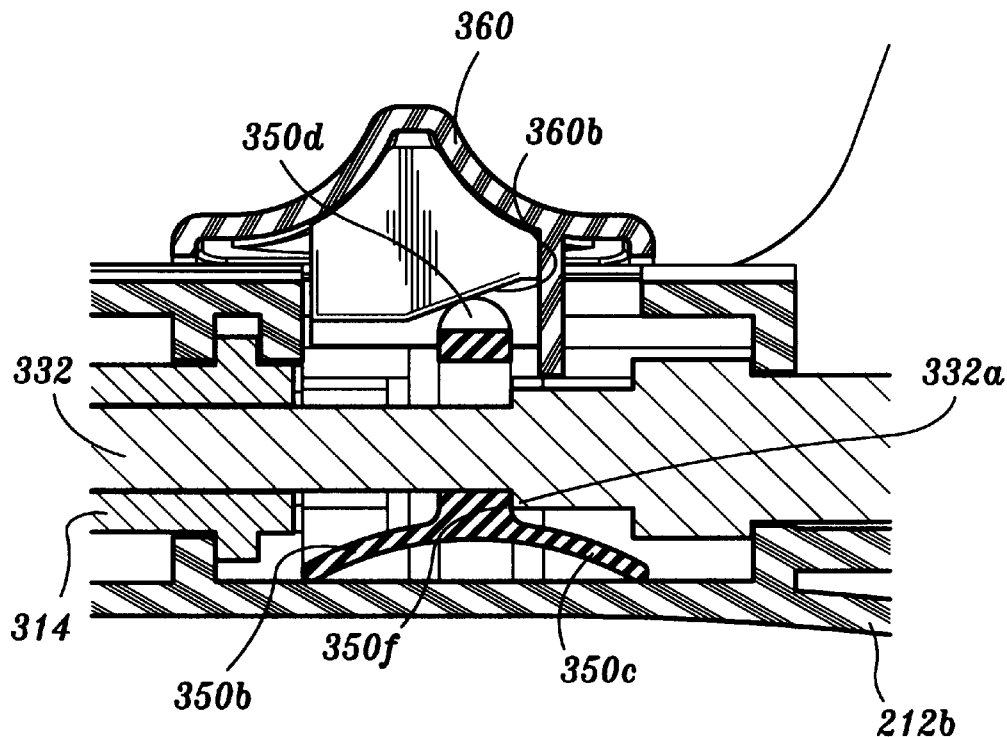
FIG. 36 is a partial cross-sectional view illustrating the initial lockout configuration of the safety firing lock-out mechanism of FIG. 32.

In the initial (pre-fired) configuration, as shown in FIG. 36, safety release slide 360 is disposed above lock spring 350 such that camming surfaces 360a and 360b contact cam following surfaces 350e and 350e, respectively, when safety release slide 360 is in the distal-most position. In this orientation, leaf spring portions 350b and 350c serve to bias lock spring 350 upwardly within the instrument housing so that a shoulder portion 332a of actuator rod 332 abuts against a proximal facing lower surface 350f, as shown in FIG. 36, to prevent firing of the instrument.

Figure 37:
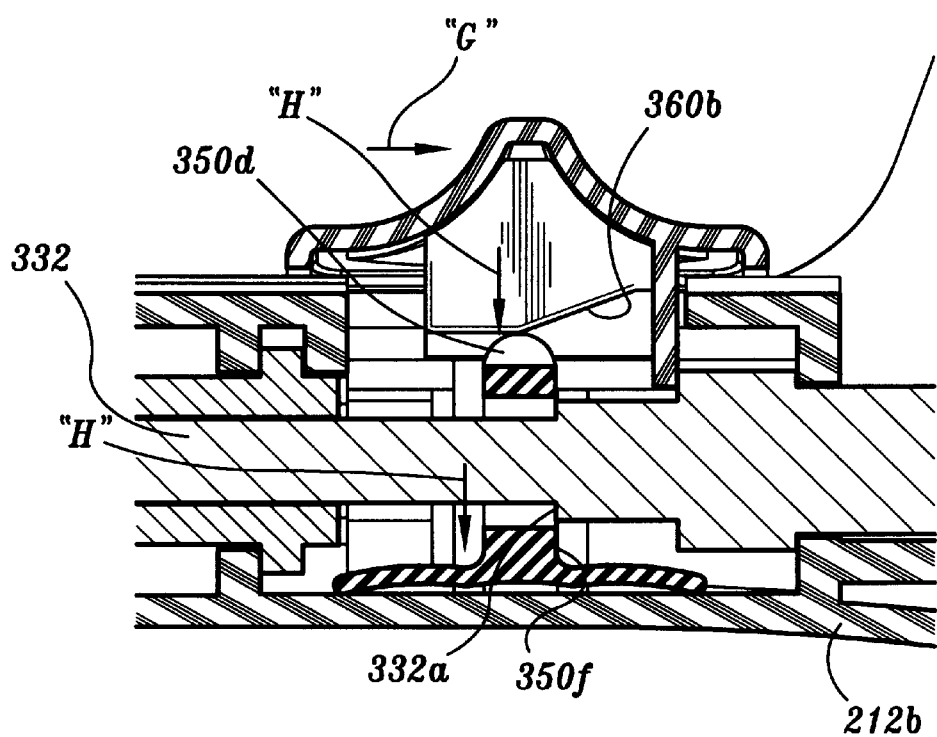
FIG. 37 is a view similar to FIG. 36, which illustrates an operational sequence of the safety firing lockout mechanism.
Figure 38:
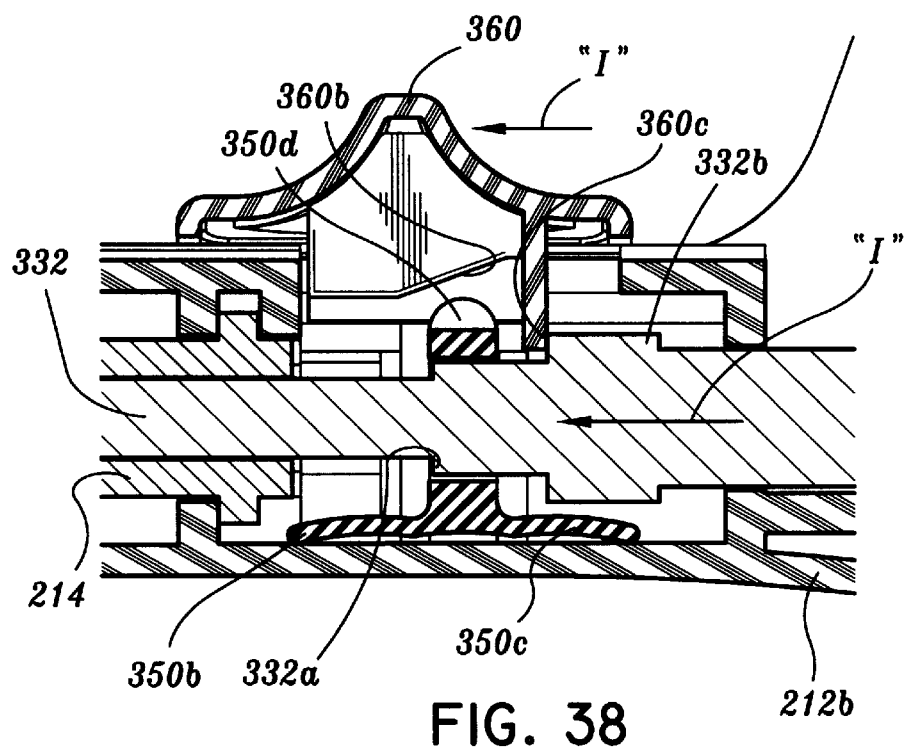
FIG. 38 is a view similar to FIG. 36 which illustrates an operational sequence of the safety firing lockout mechanism.
Figure 39:
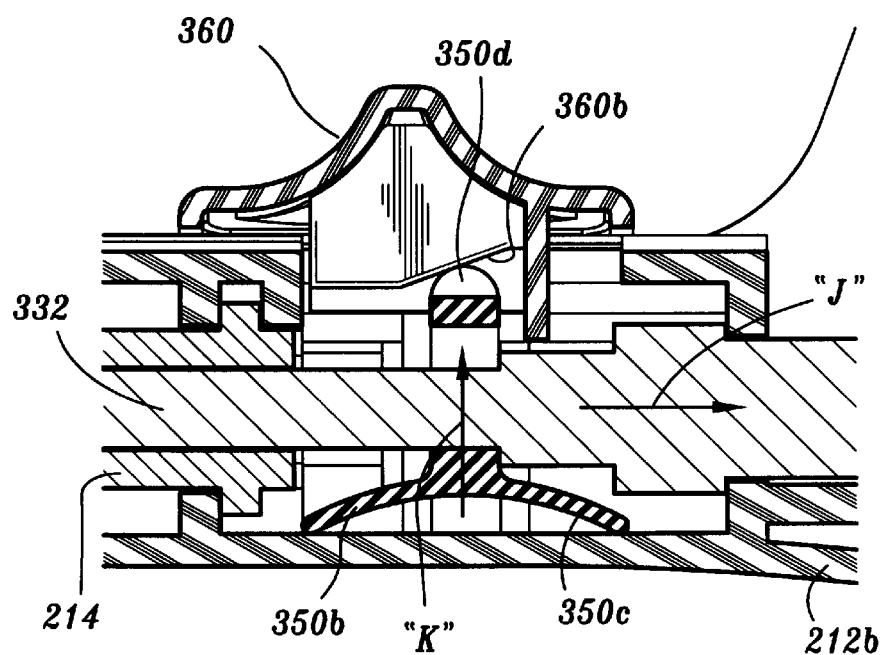
FIG. 39 is a view similar to FIG. 36 which illustrates a further operational sequential view of the safety firing lockout mechanism.

When the surgeon desires to fire the instrument, safety release slide 360 is moved proximally as indicated by arrow "G" in FIG. 37. In this manner, camming surfaces 360a and 360b travel over cam follower surfaces 350e and 350d, respectively, thereby urging lock spring 350 downwardly in the direction of arrows "H" to overcome the spring force of leaf spring portions 350b and 350c. This movement displaces proximal surface 350f below shoulder portion 332a thereby permitting actuator rod 332 to move distally. Upon distal movement of actuator rod 332 as indicated by arrow "I" in FIG. 38, a second shoulder portion 332b formed proximal of shoulder portion 332a on actuator rod 332 contacts a rear wall portion 360c of safety release slide 360 thereby urging safety release slide distally in a direction of arrow "I" as well. Upon release of actuator handle cover 246, actuator rod 332 moves proximally as indicated by arrow "J" in FIG.39 thereby permitting lock spring 350 to move upwardly as indicated by arrow "K" in FIG. 39 to reset the firing safety mechanism.

It will be understood that various modifications may be made to the embodiment shown herein. For example, the instruments may be sized to perform an anastomosis for other vessels and luminal tissue. Therefore, the above description should not be construed as limiting, but merely as exemplications of preferred embodiments. Those skilled in the art will envision other modifications within the scope and spirit of the claims appended hereto.

What is claimed is:

1. A surgical instrument for performing an anastomosis, which comprises:
   a) a housing having a proximal end and a distal end;
   b) a shaft extending from the housing distal end; and
   c) a disposable loading unit configured and dimensioned to retain a plurality of surgical fasteners, the disposable loading unit extending from the shaft and forming a juncture with the shaft, the disposable loading unit including:
      i) opposed split-sections pivotably connected to facilitate movement of the opposed split-sections between open and closed configurations, the opposed split sections being movable through a firing stroke from a first position to a second position and back to the first position to form a plurality of surgical fasteners; and
      ii) a pivot lockout member including a latch portion which extends between the opposed split-sections, the latch portion including a contact surface which interacts with a corresponding surface formed on at least one of the opposed split-sections to retain the opposed split-sections in the closed configuration, wherein upon return of the fastener pusher member to the first position from the second position, the pivot lockout member is displaced relative to the opposed split sections to an unlocked configuration.

2. A surgical instrument for performing an anastomosis according to claim 1, which further comprises a lock member disposed relative to the juncture of the disposable loading unit and the shaft, the lock member operable from the housing and movable between an unlocked position wherein the disposable loading unit is unsecured relative to the shaft and a locked position wherein the disposable loading unit is secured relative to the shaft.

3. A surgical instrument for performing an anastomosis according to claim 2 wherein the lock member is biased towards the locked position.

4. A surgical instrument for performing an anastomosis according to claim 1 which further comprises an actuator lever disposed on the housing and operatively associated with the opposed split sections such that movement of the actuator lever from an initial position to a secondary position effects movement of the opposed split sections being from the first position to the second position to effect deformation of the plurality of surgical fasteners.

5. A surgical instrument for performing an anastomosis according to claim 4 which further comprises a firing safety assembly which operatively interacts with the actuator lever to prevent unintended movement of the actuator lever from the initial position to the secondary position.

6. A surgical instrument for performing an anastomosis according to claim 5 wherein the firing safety assembly is normally biased towards a locked out configuration.

7. A surgical instrument for performing an anastomosis according to claim 1 wherein the shaft and the disposable loading unit each define respective central longitudinal axes which are substantially axially aligned with each other.

8. A surgical instrument for performing an anastomosis, which comprises:
   a) a housing having a proximal end and a distal end;
   b) a shaft extending from the housing distal end;
   c) a disposable loading unit rotatably and detachably extending from the shaft and forming ajuncture with the shaft, the disposable loading unit including:
      i) a fastener support member configured and dimensioned to support a plurality of surgical fasteners in a predetermined array of a generally close-ended geometric configuration; and
      ii) a fastener pusher member disposed adjacent the fastener support member, the fastener pusher member being movable from a first position relative to the plurality of surgical fasteners to a second position relative to the plurality of surgical fasteners so as to deform the plurality of surgical fasteners to a tissue gripping orientation;
   d) a lock member disposed relative to the juncture of the disposable loading unit and the shaft, the lock member operable from the housing and movable between an unlocked position wherein the disposable loading unit is unsecured relative to the shaft and a locked position wherein the disposable loading unit is secured relative to the shaft.

9. A surgical instrument for performing an anastomosis according to claim 8 wherein the lock member is biased towards the locked position.

10. A surgical instrument for performing an anastomosis according to claim 8 which further comprises an actuator lever disposed on the housing and operatively associated with the fastener pusher member such that movement of the actuator lever from an initial position to a secondary position effects movement of the fastener pusher member from the first position to the second position to effect deformation of the plurality of surgical fasteners.

11. A surgical instrument for performing an anastomosis according to claim 10 which further comprises an actuator rod which is connected to the actuator lever and wherein the disposable loading unit further includes an actuator member which interacts with the actuator lever to effect movement of the fastener pusher member from the first position to the second position to effect deformation of the surgical fasteners.

12. A surgical instrument for performing an anastomosis according to claim 10 which further comprises a firing safety assembly which operatively interacts with the actuator lever to prevent unintended movement of the actuator lever from the initial position to the secondary position.

13. A surgical instrument for performing an anastomosis according to claim 12 wherein the firing safety assembly is normally biased towards a locked out configuration.

14. A surgical instrument for performing an anastomosis according to claim 8 wherein the shaft and the fastener pusher member each define respective central longitudinal axes which are substantially axially aligned with each other.

15. A surgical instrument for performing an anastomosis according to claim 8 wherein the fastener support member and the fastener pusher member are each formed of respective opposing split-sections, at least two of the split-sections being pivotably connected to facilitate movement of the opposed split-sections between open and closed configurations.

16. A surgical instrument for performing an anastomosis according to claim 15 which further comprises a pivot lockout member which extends between the opposed split-sections and includes a contact surface which interacts with a corresponding surface formed on at least one of the opposed split-sections to retain the opposed split-sections in the closed configuration.

17. A surgical instrument for performing an anastomosis according to claim 16 wherein the fastener pusher member is biased to return to the first position after movement to the second position.

18. A surgical instrument for performing an anastomosis according to claim 17 wherein upon return of the fastener pusher member to the first position from the second position, the pivot lockout member is displaced to an unlocked configuration.

19. A surgical instrument for performing an anastomosis according to claim 8 wherein the disposable loading unit extends pivotably from the shaft.

20. A surgical instrument for performing an anastomosis according to claim 19 wherein the disposable loading unit is pivotable about a longitudinal axis of the shaft.

21. A disposable loading unit for a surgical anastomosis instrument, which comprises:
   a) an elongated fastener support member defining a pathway extending at least partially therethrough and including a first opening at a distal end thereof and a second opening spaced from the distal end and in communication with the pathway, the second opening configured and dimensioned to receive a tubular vessel therethrough such that the tubular vessel can pass through the pathway and extend outward from the first opening at the distal end, the fastener support member further including a plurality of spaced apart retention slots defined therein, each retention slot being adapted to support a respective surgical fastener of a plurality of surgical fasteners;
   b) a fastener pusher member disposed adjacent the fastener support member, the fastener pusher member movable from a first position relative to the plurality of surgical fasteners to a second position relative to the plurality of surgical fasteners so as to deform the plurality of surgical fasteners;
   c) an actuator operatively associated with the fastener pusher member to effect movement of the fastener pusher member from the first position to the second position; and
   d) a mounting hub disposed adjacent the actuator and defining an access opening, such that a portion of the actuator is accessible through the access opening, the mounting hub being configured and dimensioned to be removably and rotatably attached to a distal portion of the surgical instrument thereby facilitating removable attachment of the disposable loading unit to the surgical instrument.

22. A surgical instrument for performing an anastomosis according to claim 21 wherein the fastener support member and the fastener pusher member are each formed of respective opposing split-sections, at least two of the split-sections being pivotably connected to facilitate movement of the opposed split-sections between open and closed configurations.

23. A surgical instrument for performing an anastomosis according to claim 22 which further comprises a pivot lockout member which extends between the opposed split-sections and includes a contact surface which interacts with a corresponding surface formed on at least one of the opposed split-sections to retain the opposed split-sections in the closed configuration.

24. A surgical instrument for performing an anastomosis according to claim 23 wherein the fastener pusher member is biased to return to the first position after movement to the second position.

25. A surgical instrument for performing an anastomosis according to claim 24 wherein upon return of the fastener pusher member to the first position from the second position, the pivot lockout member is displaced to an unlocked configuration.

26. A method of performing a vascular anastomosis comprising the steps of:
   a) providing a disposable loading unit having a fastener support member defining a passage therethrough for reception of a first vessel, a plurality of surgical fasteners supported by the fastener support at a distal end thereof;
   b) positioning an end of the first vessel through the passage and everting the end of the vessel over the distal end of the fastener support adjacent the plurality of surgical fasteners;

c) engaging the first vessel with the surgical fasteners;

d) inserting the distal edge of the fastener support into an opening in a side wall of a second vessel;

e) engaging the side wall of the second vessel with the surgical fasteners adjacent the opening;

f) connecting the disposable loading unit to an actuator handle assembly after step e) such that the disposable loading unit is rotatable with respect to the actuator handle assembly; and g) deforming the legs of each surgical fastener by actuation of the actuator handle assembly to secure the first and second vessels together in fluid communication with each other.

27. A method of performing a vascular anastomosis according to claim 26, which further comprises the step of removing the first vessel from the disposable loading unit by opening a split-section of the disposable loading unit.

* * * * *

UNITED STATES PATENT AND TRADEMARK OFFICE
CERTIFICATE OF CORRECTION

PATENT NO. : 6,083,234
DATED : July 4, 2000
INVENTOR(S) : David A. Nicholas et al.

It is certified that error appears in the above-identified patent and that said Letters Patent is hereby corrected as shown below:

Title page,
Item [75], Amend inventorship as follows: David A. Nicholas, Trumbull; Robert C. Smith, Shelton; and Scott E. Manzo, Shelton, all of Conn.

Item [73], change "Surgical Dynamics, Inc." to -- United States Surgical Corporation --

Signed and Sealed this

Twenty-third Day of April, 2002

*Attest:*

JAMES E. ROGAN
*Attesting Officer*    *Director of the United States Patent and Trademark Office*